(12) United States Patent
Vargas Fonseca

(10) Patent No.: US 12,005,247 B2
(45) Date of Patent: Jun. 11, 2024

(54) PUMP FOR ARTIFICIAL CIRCULATORY ASSISTANCE AND A PUMPING SYSTEM

(71) Applicant: ZAMMI INSTRUMENTAL LTDA, Duque de Caxias (BR)

(72) Inventor: Luiz Henrique Vargas Fonseca, Duque de Caxias (BR)

(73) Assignee: ZAMMI INSTRUMENTAL LTDA, Duque de Caxias (BR)

( * ) Notice: Subject to any disclaimer, the term of this patent is extended or adjusted under 35 U.S.C. 154(b) by 1392 days.

(21) Appl. No.: 16/338,446

(22) PCT Filed: Sep. 29, 2017

(86) PCT No.: PCT/BR2017/050292
§ 371 (c)(1),
(2) Date: Mar. 29, 2019

(87) PCT Pub. No.: WO2018/058226
PCT Pub. Date: Apr. 5, 2018

(65) Prior Publication Data
US 2020/0038565 A1   Feb. 6, 2020

(30) Foreign Application Priority Data

Sep. 29, 2016   (BR) .......................... 102016022713-5

(51) Int. Cl.
*A61M 1/00*  (2006.01)
*A61M 1/36*  (2006.01)
(Continued)

(52) U.S. Cl.
CPC ........ *A61M 60/435* (2021.01); *A61M 1/3666* (2013.01); *A61M 60/113* (2021.01);
(Continued)

(58) Field of Classification Search
CPC .......... A61M 1/3666; A61M 2205/103; A61M 2205/106; A61M 39/24; A61M 5/14224;
(Continued)

(56) References Cited

U.S. PATENT DOCUMENTS 3,656,873 A * 4/1972 Schiff ................... A61M 60/38
623/3.1
3,883,272 A   5/1975 Puckett
(Continued)

FOREIGN PATENT DOCUMENTS

WO    2015179929 A1   12/2015

OTHER PUBLICATIONS

International Search Report issued in International Application No. PCT/BR2017/050292, dated Dec. 1, 2017 (2 pages).
(Continued)

*Primary Examiner* — Dirk R Bass
(74) *Attorney, Agent, or Firm* — Osha Bergman Watanabe & Burton LLP

(57) ABSTRACT

Membranes are provided to be specially developed for use in chambers for artificial circulatory assistance which may be employed primarily in cardiovascular procedures, notably to produce arterial capacitance, to regulate blood pressure, to produce aortic counterpulsation and to pump blood. The membrane may have circular sections that may vary in size or not depending on the function to be performed and are interconnected so that the transition between one section and the other is smooth, regardless of the size of each section. Further, chambers and pumps may be used for cardiopulmonary bypass and a pumping system.

25 Claims, 15 Drawing Sheets

(51) Int. Cl.
    *A61M 60/113*     (2021.01)
    *A61M 60/148*     (2021.01)
    *A61M 60/178*     (2021.01)
    *A61M 60/258*     (2021.01)
    *A61M 60/268*     (2021.01)
    *A61M 60/36*     (2021.01)
    *A61M 60/43*     (2021.01)
    *A61M 60/435*     (2021.01)
    *A61M 60/441*     (2021.01)
    *A61M 60/523*     (2021.01)
    *A61M 60/531*     (2021.01)
    *A61M 60/554*     (2021.01)
    *A61M 60/894*     (2021.01)
    *F04B 19/06*     (2006.01)
    *F04B 43/02*     (2006.01)
    *A61M 39/24*     (2006.01)

(52) U.S. Cl.
CPC ........ *A61M 60/148* (2021.01); *A61M 60/178* (2021.01); *A61M 60/258* (2021.01); *A61M 60/268* (2021.01); *A61M 60/36* (2021.01); *A61M 60/43* (2021.01); *A61M 60/441* (2021.01); *A61M 60/523* (2021.01); *A61M 60/531* (2021.01); *A61M 60/554* (2021.01); *A61M 60/894* (2021.01); *F04B 19/06* (2013.01); *A61M 39/24* (2013.01); *A61M 2205/103* (2013.01); *A61M 2205/106* (2013.01)

(58) Field of Classification Search
CPC .............. A61M 60/113; A61M 60/148; A61M 60/178; A61M 60/258; A61M 60/268; A61M 60/36; A61M 60/43; A61M 60/435; A61M 60/441; A61M 60/523; A61M 60/531; A61M 60/554; A61M 60/869; A61M 60/894; A61M 60/896; F04B 19/06; F04B 39/005; F04B 43/0733; F04B 43/084; F04B 43/1253; F16K 15/14; F16K 15/144
See application file for complete search history.

(56) References Cited

U.S. PATENT DOCUMENTS

| | | | |
|---|---|---|---|
| 4,047,844 A * | 9/1977 | Robinson .............. | F04B 43/082 417/63 |
| 7,273,465 B2 | 9/2007 | Ash | |
| 2003/0220607 A1* | 11/2003 | Busby ..................... | A61M 1/28 210/252 |
| 2007/0253463 A1* | 11/2007 | Perry ...................... | F04B 13/02 374/208 |
| 2009/0099498 A1* | 4/2009 | Demers ............... | A61M 60/531 604/4.01 |
| 2009/0137940 A1* | 5/2009 | Orr ..................... | A61M 60/554 604/82 |
| 2013/0343936 A1* | 12/2013 | Gray ..................... | G05D 16/20 417/437 |
| 2016/0208940 A1* | 7/2016 | Vargas Fonseca ........................... A61M 5/16804 | |
| 2017/0112984 A1 | 4/2017 | Vargas Fonseca | |
| 2017/0197047 A1* | 7/2017 | Minato ............. | A61M 16/0078 |

OTHER PUBLICATIONS

Written Opinion issued in International Application No. PCT/BR2017/050292; dated Dec. 5, 2017 (7 pages).

International Preliminary Report on Patentability issued in International Application No. PCT/BR2017/050292 dated Jan. 4, 2019 (3 pages).

* cited by examiner

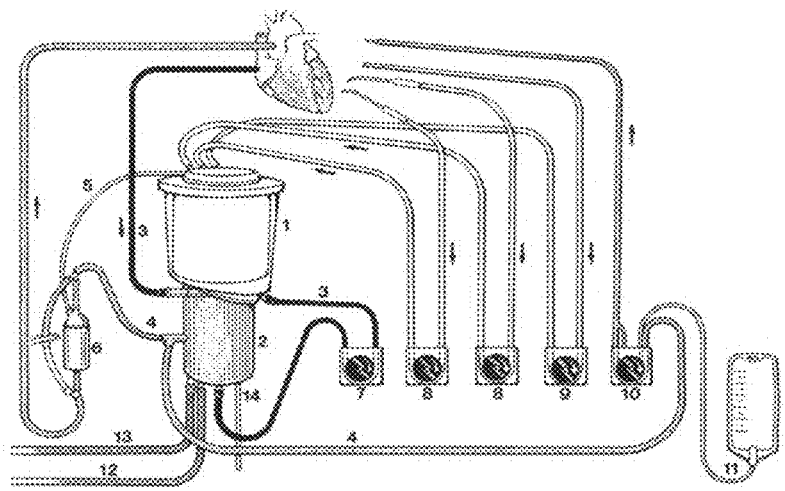
FIG. 1 (*Prior Art*)
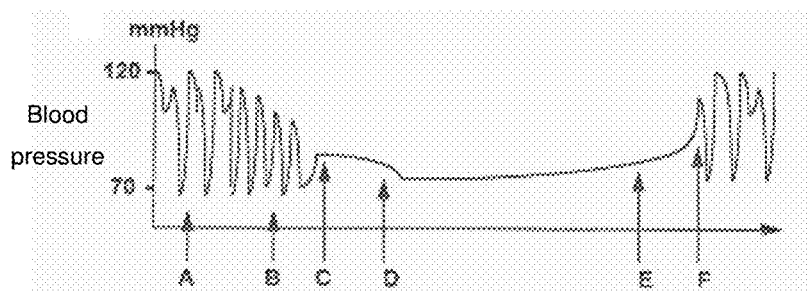
FIG. 2 (*Prior Art*)
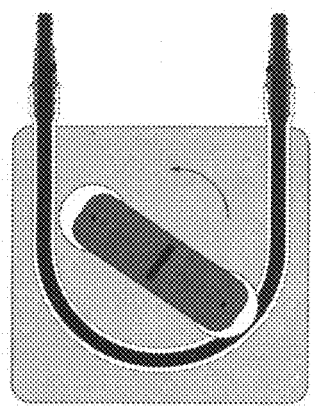
FIG. 3 (*Prior Art*)

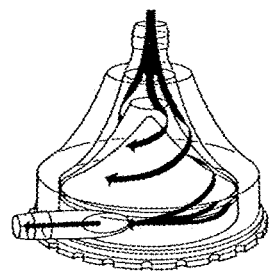
FIG. 4 (*Prior Art*)
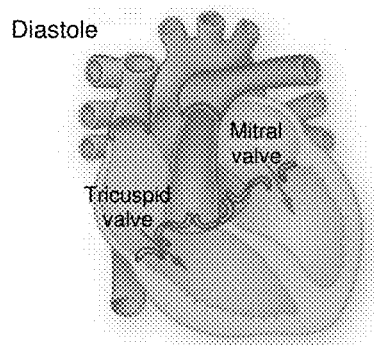
FIG. 5a (*Prior Art*)
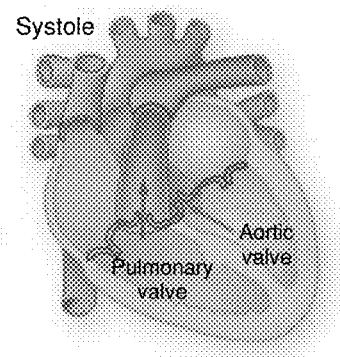
FIG. 5b (*Prior Art*)
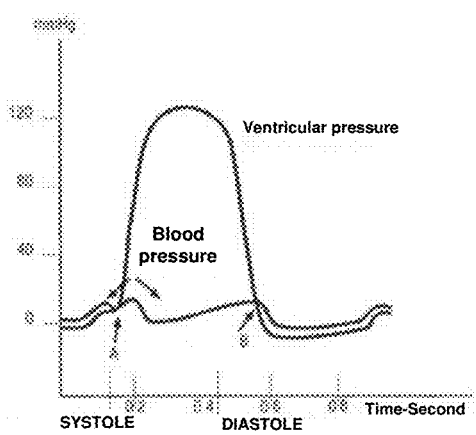
FIG. 6a (*Prior Art*)
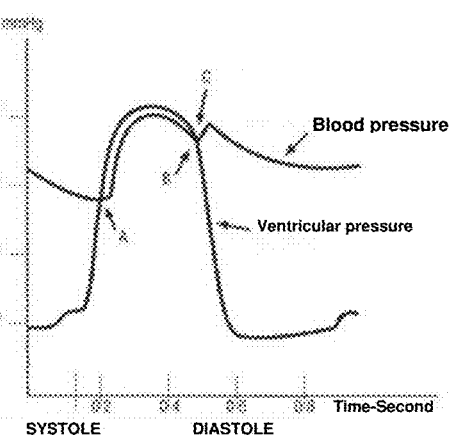
FIG. 6b (*Prior Art*)

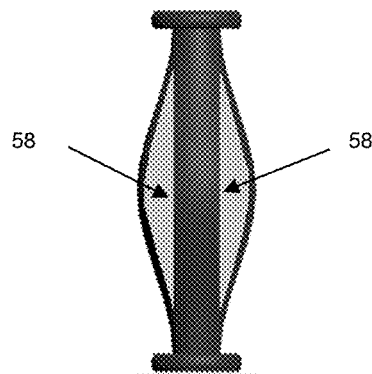
FIG. 7a (*Prior Art*)
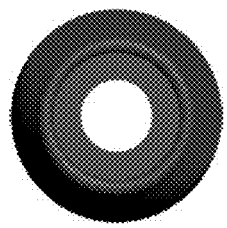
FIG. 7b (*Prior Art*)
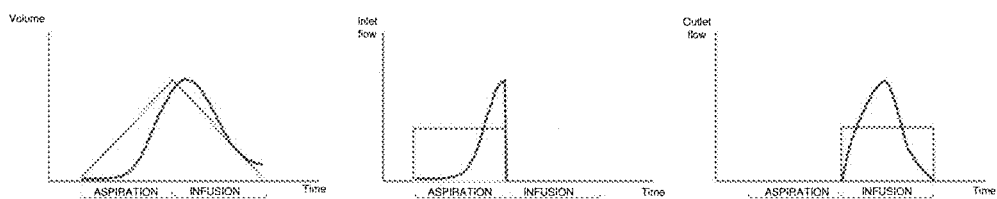
FIG. 8A (*Prior Art*)   FIG. 8B (*Prior Art*)   FIG. 8C (*Prior Art*)

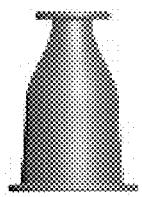 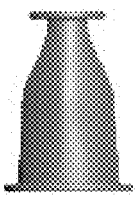 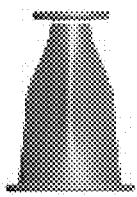 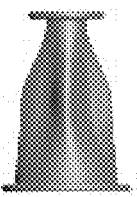 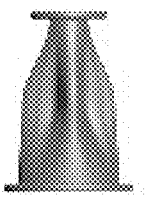 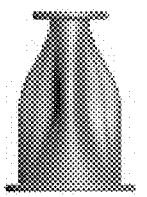
FIG. 12Aa  FIG. 12Ba  FIG. 12Ca  FIG. 12Da  FIG. 12Ea  FIG. 12Fa
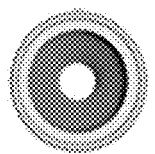 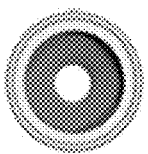 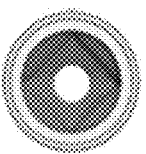 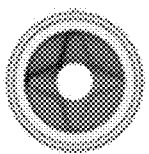 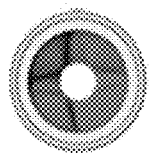 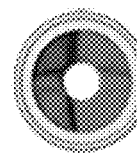
FIG. 12Ab  FIG. 12Bb  FIG. 12Cb  FIG. 12Db  FIG. 12Eb  FIG. 12Fb
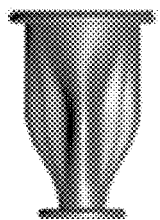 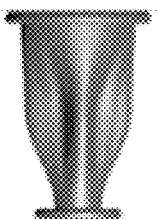 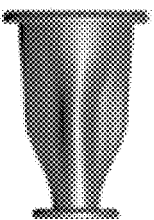 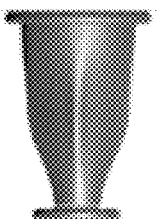 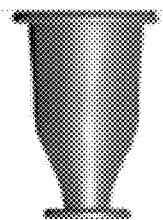 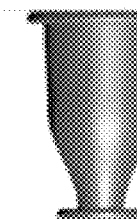
FIG. 13Aa  FIG. 13Ba  FIG. 13Ca  FIG. 13Da  FIG. 13Ea  FIG. 13Fa
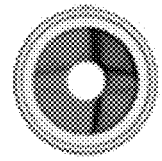 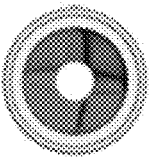 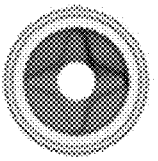 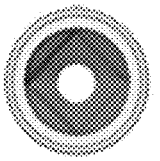 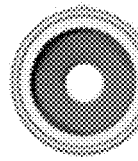 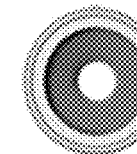
FIG. 13Ab  FIG. 13Bb  FIG. 13Cb  FIG. 13Db  FIG. 13Eb  FIG. 13Fb

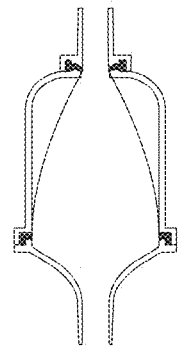
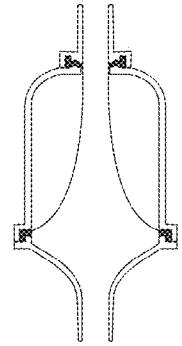
FIG. 14A  FIG. 14B
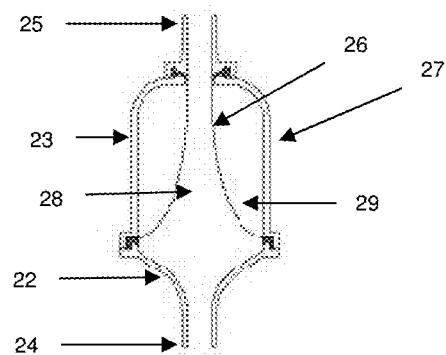
FIG. 15
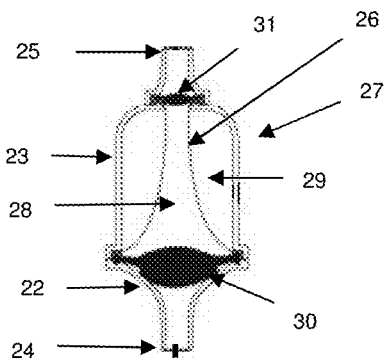
FIG. 16

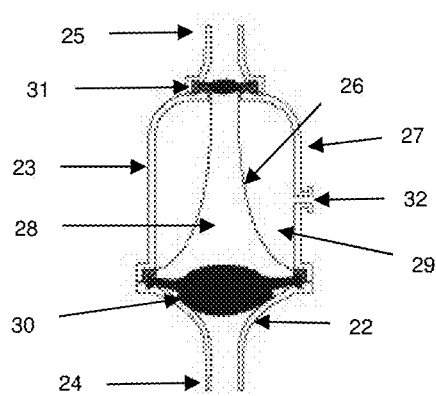
FIG. 17
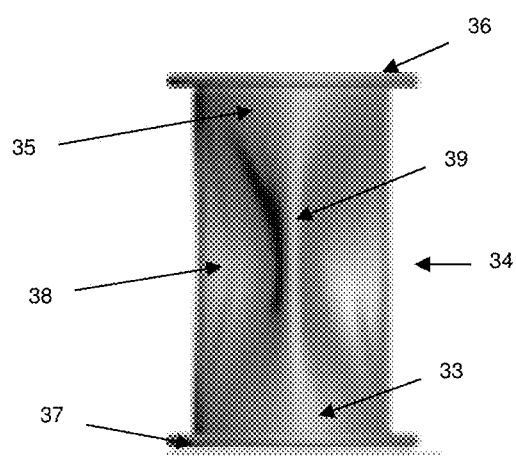
FIG. 18
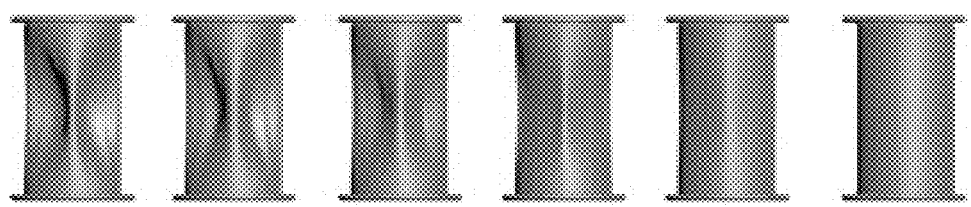
| FIG. 19Aa | FIG. 19Ba | FIG. 19Ca | FIG. 19Da | FIG. 19Ea | FIG. 19Fa |
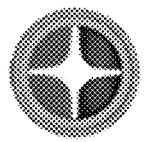 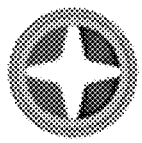  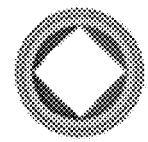 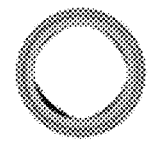 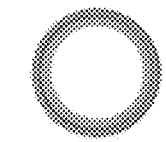
FIG. 19Ab   FIG. 19Bb   FIG. 19Cb   FIG. 19Db   FIG. 19Eb   FIG. 19Fb

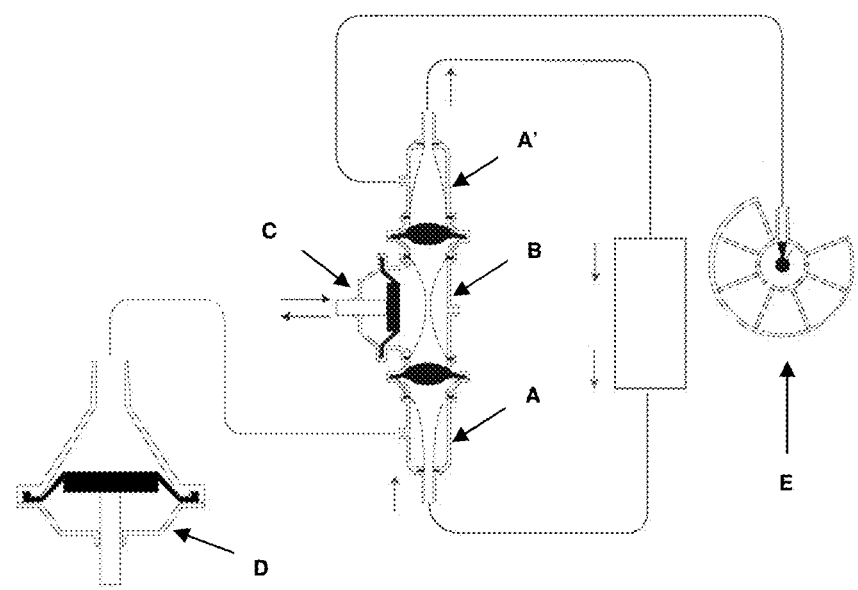
FIG. 26
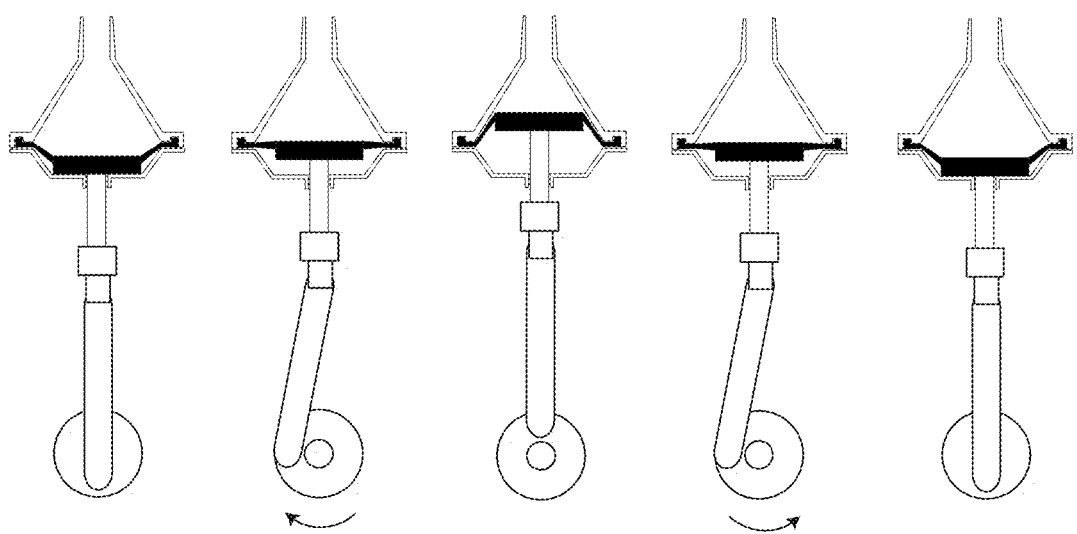
FIG. 27A  FIG. 27B  FIG. 27C  FIG. 27D  FIG. 27E

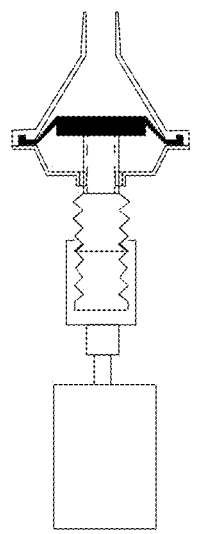 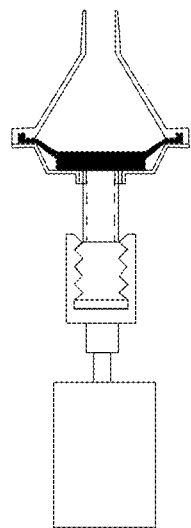 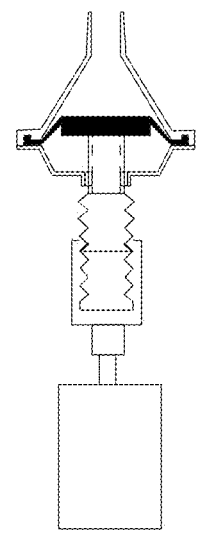
FIG. 28A  FIG. 28B  FIG. 28C
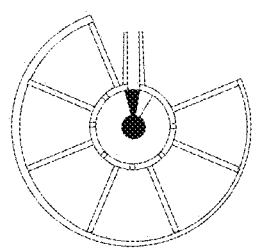 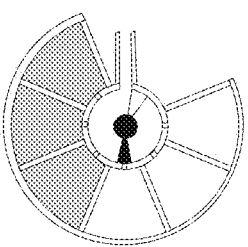 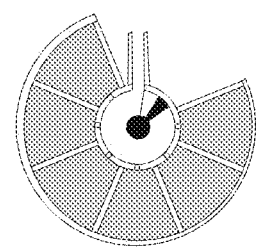
FIG. 29A  FIG. 29B  FIG. 29C

PUMP FOR ARTIFICIAL CIRCULATORY ASSISTANCE AND A PUMPING SYSTEM

FIELD OF THE INVENTION

The present invention relates to membranes specially developed for use in chambers for artificial circulatory assistance which may be employed primarily in cardiovascular procedures, notably to produce arterial capacitance, to regulate blood pressure and to produce aortic counterpulsation.

The present invention further relates to the above-mentioned chambers, pumps for cardiopulmonary bypass and a pumping system. The chambers and membranes according to the present invention can be applied as implantable, provisional or definitive medical devices to act as a cardiovascular orthosis or prosthesis with functions of, among others, peak blood pressure damping, blood pumping and generation of arterial line complacency of cardiopulmonary bypass circuit during cardiovascular surgical procedures requiring the use of this technique, active circulatory assistance (VAD), aortic counterpulsation action, optimization of aortic complacency in patients with refractory arterial hypertension and with reduced arterial distensibility, pumping device for cavity drainage and pumping device for cavity aspiration.

BACKGROUND OF THE INVENTION

Arterial hypertension is a polygenic syndrome and comprises genetic, environmental, vascular, hormonal, renal and neural aspects. Essential or primary arterial hypertension (AH) is one of the most common causes of cardiovascular disease, affecting approximately 20% of the adult population in industrialized societies. The disease is a risk factor for the development of coronary disease, accelerates the process of atherosclerosis and may be a determining factor for the premature emergence of cardiovascular morbidity and mortality associated with coronary disease, congestive heart failure, stroke and end-stage renal disease.

Therapy for arterial hypertension contributes to the reduction of cardiovascular morbidity and mortality. In general, blood pressure values to be achieved with treatment are: BP<130/80 mmHg in the general population and BP<140/90 mmHg for diabetic hypertensive or nephropathic patients. To reach this goal in terms of blood pressure level, non-pharmacological and pharmacological measures are applied. However, when the goal is not reached even with the simultaneous use of at least three antihypertensive drugs of different classes, hypertension is classified as refractory.

In this scenario, the percutaneous approach to bilateral renal sympathetic denervation (RSD) using a catheter coupled to a radiofrequency device has been used as an available therapeutic strategy. The technique is based on the knowledge that, among the various pathophysiological mechanisms involved in the refractoriness of AH control, the excessive stimulation of the renal sympathetic nervous system stands out.

This type of device produces radiofrequency shots that are applied to the renal artery wall by means of a catheter. Several models of these devices have been developed to perform the DSR, but the absence of more comprehensive studies on the cost-effectiveness of the procedure makes it impossible to recommend them on a large scale and is therefore only indicated for true resistant hypertensive patients, a very high cardiovascular risk group.

Cardiopulmonary bypass (CPB) is a technique employed in cardiovascular procedures allowing temporary replacement of cardiopulmonary functions. The heart pumping functions are performed by a mechanical pump and the lung functions are replaced by a device capable of performing the gas exchanges with the blood interconnected in series by a circuit of plastic tubes. FIG. 1 depicts a basic circuit of cardiopulmonary bypass with membrane oxygenator comprising cardiotomy reservoir (1), oxygenation chamber (2), venous line (3), arterial line (4), arterial line filter return (5), arterial filter (6), arterial pump (7), aspirator pumps (8), ventricular decompression pump (9), cardioplegia pump (10), crystalloid cardioplegia (11), water inlet line (12), water outlet line (13) and gas line (14). This is a cardiopulmonary bypass circuit, the structure and functioning of which is classically known to those skilled in the art.

Cardiopulmonary bypass is known to be a procedure governed by physiological principles, which under certain circumstances may be necessary for periods of 1 hour, 2 hours and even weeks. In these cases, the deviations of physiology are more pronounced and, consequently, they bring more complications to the organism. The great functional differences between the human organism and the artificial organs are reflected in the reactions of the human organism during and shortly after CPB. Hundreds of surgeries are performed daily all over the world. Recovery without consequences is the rule. However, certain patients may present with important complications caused by hypoxia, embolisms, coagulopathies and blood dyscrasias, cerebral edema or of other organs, as well as changes related to the exacerbated response of the body's protection and defense systems that can produce intercurrences of different levels of implications and may act on pre-existing morbidities and even lead to death.

The high resistance to the flow generated by the membrane in the oxygenation chamber traumatizes the blood and activates platelets. The long circuits of CPB require large filling volumes (prime), which leads to hemodilution of blood, which, when poorly sized, affects oxygen transport, excessively reduces blood viscosity and oncotic pressure, which, associated to the continuous flow produced by non-pulsatile flow pumps, leads to change of capillary permeability and consequent formation of interstitial edema.

FIG. 2 graphically shows the behavior of blood pressure to show that mechanical pumping produces a linear flow, i.e. without the occurrence of pulsation. In this figure the pre-by-pass phase (A.1), the partial by-pass period (B.1), the total bypass (C.1), the period between (C.1) and (D.1) corresponding to the blood hypotension at the beginning of the perfusion. It is also observed that blood pressure stabilizes until the elevation is initiated by the action of catecholamines and other natural vasopressors and indicates a more pronounced elevation of blood pressure after 30 or 40 minutes of perfusion, being then observed the perfusion outlet (F.1).

The control mechanisms of the pulse wave sensitive receptors are absent in the CPB with linear flow. The absence of the arterial pulse triggers a series of events culminating in the release of vasoactive substances into the blood flow, determining the closure of arterioles and reduction of perfusion in the capillary periphery, which results in the induction of a syndrome identified as Organism Inflammatory Response Syndrome and poor tissues perfusion.

The traditional CPB technique basically consists of simulation of the circulatory system connected to an oxygenator device capable of promoting gas exchange in the blood, removing carbon dioxide and supplying oxygen and heating the blood through a heat exchanger coupled to the oxygenator device. This circuit is mounted on a heart-lung machine. The system is prepared and connected to the patient in parallel to the normal circulatory system, by venous-arterial access. The circuit is connected to the venous access by a tube inserted into the right atrium or by two tubes in the inferior and superior vena cava. Blood is drained from the opening of the venous line to the venous reservoir, blood volume accumulating device, and then arrives at the blood pumping device that produces adequate blood flow to the needs of the patient. The blood then reaches the oxygenator which has coupled it with a heat exchange system allowing manipulating the temperature of the flow passing through it. The temperature exchange occurs before the blood reaches the oxygenation chamber where it undergoes gas exchange. Oxygenation chamber contains an amount of microporous and hollow microfibers that are traversed internally by the flow of the oxygen-enriched air mixture and is traversed externally by blood flow. A continuous supply of oxygen-enriched air mixture is attached to the oxygenation chamber, delivering oxygen to the blood while simultaneously removing excess carbon dioxide. After oxygenation, blood returns to the normal arterial circulation through an arterial access tube.

Specifically, the blood pumping is performed by a mechanical peristaltic drive pump. A segment of the collapsible circuit is mounted in the roller pump housing. The rollers are disposed at an angle of 180° to each other in a semicircular housing 210° angle and are adjusted to compress the segment of tubes in its course on it so that when compressing the tube, it pushes its contents from a point A to a point B.

FIG. 3 depicts this two-roller pump which has been adopted because of its mechanical simplicity, ease of construction and use, and the safety it offers. The flow generated by it is not pulsatile linear. The pump is electrically operated but can also be manually actuated by handles attached to the roller axis in the event of electrical or mechanical failure of the equipment. If not used properly, the roller pump can aspirate and pump air, generating extremely serious complications. Adjusting the distance between the roller and the rigid bed in which its travels is critical for proper pump operation and is called roller calibration. The calibration point is the occlusive point of the tube segment. Another disadvantage of using such a pump is the high negative pressure exerted on the inlet hole to aspirate the liquid to be propelled. An excessively tight roller, in addition to the occlusive point, increases blood trauma and may lead to marked hemolysis. An excessively handily roller allows reflux, causes eddy and hemolysis, in addition to drives variable blood volumes according to the resistance status of the perfused arteriolar system.

An alternative to the roller pump provided by the prior art is the centrifugal pump shown in FIG. 4. The centrifugal pump is known as a kinetic pump, i.e. a pump in which the action of blood propulsion is performed by the addition of kinetic energy produced by the rotations of a rotor element. In the most common type of centrifugal pump, there is a set of concentric cones, of which the outermost of polycarbonate contains a central inlet hole and a side outlet hole, to which the corresponding lines are adapted. The innermost cone has a magnetic coupling with an external rotor that rotates it at high rotations per minute. The rotation of the inner cone rotates the other cones. This produces a vortex effect and its transmission produces blood flow. In this type of pump, it is noted that the drawback of hemolysis production remains present, as in modern roller pumps, and under certain conditions it can also propel the air. Another aspect to be considered is that in this pump there is no preload and the flow depends directly on the number of revolutions per minute of the internal cone. The flow varies depending on the peripheral vascular resistance against which the pump drives the blood. When the spinning speed of the cone is decreased, the blood flow is reduced; when the patient's peripheral resistance increases, the pump flow also decreases. If the constant speed (rpm) is maintained and the patient's peripheral vascular resistance is reduced, the blood flow will increase substantially. For proper operation control of this type of pump, a flowmeter coupled to the system is essential. The pump flow cannot be evaluated otherwise.

As noted, both types of pumps described above are currently employed in CPB as a blood pumping device, however, both are linear or continuous blood flow generating propellants.

The blood flow is physiologically pulsatile and morphologically a result of the cardiac cycle. Briefly, the cardiac cycle comprises a systole (contraction) and a diastole (relaxation). The contraction and relaxation of the heart chambers result in changes in pressure within thereof, which produce blood movement through the cardiovascular system, as shown in FIG. 4. Cyclically, the blood that reaches the heart's vena cava accumulates in the right atrium after opening the tricuspid valve, reaches the right ventricle in its relaxation phase, after filling, the ventricle contracts, the tricuspid valve closes, and the pulmonary valve opens directing the blood flow to the pulmonary artery. Blood travels to the lungs and returns through the pulmonary veins that converge in the left atrium and reaches the left ventricle through the opening of the mitral valve. The contraction of the left ventricle closes the mitral valve and opens the aortic valve, determining blood flow to the systemic circulation, contraction of the myocardium, closure and opening of valves, the volume of blood ejected into the systemic circulation. This cycle produces a large variation in blood pressure, i.e. the pressure wave.

At each cardiac cycle a quantity of blood is ejected into the arteries (systolic volume) and the frequency of cycles produces cardiac output, the intensity of which produces blood flow in the arteries and, at the same time, determines a force contrary to flow, called resistance. The relationship between flow and resistance determines blood pressure. Blood pressure has wave morphology with pressure peaks (systolic pressure) and wave depression (diastolic pressure). The difference in systolic and diastolic pressure is the arterial pulse.

As an attempt to make the flow more similar to the heart reciprocating pump flow, several researchers have proposed changes to conventional pumps to provide pulsatile flow. In terms of hemodynamics and metabolic behavior, the undesirable effects of linear flow are reduced or eliminated by the pulsatile flow perfusion. There is a solid theoretical and experimental basis demonstrating the advantages of pulsatile flow in cardiopulmonary bypass. The main reasons for a better pulsatile flow tissue perfusion are pulse wave energy, capillary closure pressure, and pulse wave-sensitive receptor control mechanisms. The energy of the pulse wave is important in its transmission to the capillaries of the tissues, favoring tissue perfusion, while the diastolic phase of the pulse pressure keeps the capillaries open for a longer time, favoring the fluid exchanges with the interstitial fluid. Several receptors of the arterial system depend on the variations of the pressure and the pulse wave to emit regulating stimuli of the vascular tone and the release of hormones. These factors are, to some extent, responsible for the increase of peripheral arterial resistance that occurs in perfusion with linear flow. Several experimental and clinical studies have shown that cerebral, renal, and various other organ perfusion is superior with pulsatile flow, which also produces less metabolic acidosis and maintains vascular resistance normal.

FIG. 6a shows a graph demonstrating the behavior of intraventricular and atrial pressures during the cardiac cycle. Point (A) indicates the closure of the atrioventricular valves and point (B) indicates the moment of its opening. FIG. 6b shows a graph demonstrating the behavior of left and aortic ventricular pressures during the cardiac cycle. Point (A) indicates the moment of opening of the aortic valve and point (B) is the moment of closure, which determines a notch in the aortic pressure curve.

Other studies and practical experiments demonstrate that the arterial tube hole reduces the transmission of the pulse wave to the patient's circulatory system, in addition to accentuating cellular trauma and hemolysis. Several mechanisms were developed as an attempt to produce viable pulsatile flow, however, for the most part, no effective comparative advantages were established with the linear pumping system, due, for the most part, to include a pulse producing device in the CPB circuit line, although the pumping is performed by a linear flow pump. Patent application PI0803331-5A2 depicts properly this attempt.

U.S. Pat. No. 3,883,272 is the closest prior art document to the present invention. The patent describes a reusable pump that allows its disposable internal parts to be replaced. However, the mechanism for assembling and replacing parts is not simple, as the parts must be assembled in a specific sequence and if improperly assembled, they can result in malfunctions.

In addition, the described pump utilizes ball valves which are dependent on the spatial position of the product and may lock, being permanently open or closed, which is extremely detrimental to the blood flow in the subject.

Other problems presented by this type of pump are related to the use of membranes made of elastic material. In this type of membrane, when the air is aspirated from the external chamber, in order to the blood enters the chamber, the membrane must be dilated (FIG. 7a). Therefore, dilation will only occur when the force applied to overcome the elastic force exceeds a certain value. This effect occurs abruptly and uncontrolled resulting in a marked peak of flow and pressure, both at the inlet and at the outlet, can cause collapse of the veins and even hemolysis or interruption of the flow and ischemia due to lack of oxygenation.

Membranes made of elastic material are also subject to loss or change of their performance or even rupture due to the wear caused by the constant dilation suffered by the continuous use of the membrane.

Another major disadvantage presented by the elastic membranes and consequently the systems that use it is the formation of stagnation points when used as pressure dampers, which can cause blood clotting at points wherein there is no flow and volume is stagnant (58), and may result in a variety of complications, such as formation and release of thrombi into the patient's circulation.

Accordingly, it is the object of the present invention to provide a membrane applicable to chambers for artificial circulatory assistance which effectively addresses the prior art problems discussed above, in addition to advantageously providing the supply of pulsed pump CPB and can be used beneficially in patients suffering from systemic arterial hypertension refractory to currently available treatments.

BRIEF DESCRIPTION OF THE DRAWINGS

The present invention will now be described with reference to the other accompanying drawings which, in a schematic and non-limiting way of its scope, represent:

FIG. 1 depicts a basic circuit of cardiopulmonary bypass with membrane oxygenator available from the prior art.

FIG. 2 depicts graphically the behavior of blood pressure in a pumping system available from the prior art.

FIG. 3 depicts a cross-sectional front view of a two-roller pump available from the prior art.

FIG. 4 depicts a schematic cross-sectional view of a roller-type centrifugal pump available from the prior art.

FIGS. 5*a* and 5*b* depict schematic cross-sectional views of the physiological cardiac blood flow available from the prior art.

FIG. 6*a* graphically depicts the behavior of intraventricular and atrial pressures during the cardiac cycle available from the prior art.

FIG. 6*b* graphically depicts the behavior of left and aortic ventricular pressures during the cardiac cycle available from the prior art.

FIG. 7*a* depicts a front view of a membrane made of elastic material available from the prior art.

FIG. 7*b* depicts a top view of a membrane made of elastic material available from the prior art.

FIGS. 8A-8C graphically depict the behavior of the inflow and outflow and the volume in the aspiration and infusion phase when a membrane made of elastic material is used, available from the prior art.

FIGS. 12A*a*-12F*a* depict front and bottom views of the variation of the membrane shape to be used for negative arterial pulse wave dampening according to the present invention, based on its internal volume, from the rest state "Aa" with maximum membrane capacity up to "Fa" state with minimum membrane capacity.

FIGS. 12A*b*-12F*b* depict bottom views of the variation of the membrane shape to be used for negative arterial pulse wave dampening according to the present invention, based on its internal volume, from the rest state "Ab" with maximum membrane capacity up to "Fb" state with minimum membrane capacity.

FIGS. 13A*a*-13F*a* depict front and bottom views of the variation of the shape of a variant form of the membrane to be used for positive arterial pulse wave dampening in accordance with the present invention, based on its internal volume, starting from rest state "Aa" with minimum membrane capacity to state "Fa" with maximum membrane capacity.

FIGS. 13A*b*-13F*b* depict bottom views of the variation of the shape of a variant form of the membrane to be used for positive arterial pulse wave dampening in accordance with the present invention, based on its internal volume, starting from rest state "Ab" with minimum membrane capacity to state "Fb" with maximum membrane capacity.

FIGS. 14A and 14B depict schematic cross-sectional views of the variation of the membrane shape to be used for arterial pulse wave dampening according to the present invention, with FIG. 14A being the maximum capacity and FIG. 14B the minimum capacity of membrane volume.

FIG. 15 depicts a schematic cross-sectional view of the circulatory assist chamber comprising the membrane according to the present invention, detailing each component.

FIG. 16 depicts a schematic cross-sectional view of a first variant form of the artificial circulatory assist chamber according to the present invention.

FIG. 17 depicts a schematic cross-sectional view of a second variant form of the artificial circulatory assist chamber according to the present invention.

FIG. 18 depicts a front view of the pumping membrane according to the present invention.

FIGS. 19A$a$-19F$a$ depict front and top views of the shape variation of the membrane for pumping according to the present invention based on its internal volume, starting from the rest state "Aa" with minimum membrane capacity up to the state "Fa" with maximum membrane capacity.

FIGS. 19A$b$-19F$b$ depict top views of the shape variation of the membrane for pumping according to the present invention based on its internal volume, starting from the rest state "Ab" with minimum membrane capacity up to the state "Fb" with maximum membrane capacity.

FIG. 23$b$ graphically depicts the behavior of the inflow and outflow during the aspiration and infusion phase for the pulsatile pumping device provided with a membrane-equipped dampening chamber described in the present invention.

FIG. 26 depicts a schematic cross-sectional view of the complete pumping system shown in FIG. 24, in a preferred variant embodiment.

FIGS. 27A-27E depict schematic cross-sectional views of the reversible movement of the piston of the air pump C.

FIGS. 28A-28C depict schematic cross-sectional views of the movement of the piston of pump D.

FIGS. 29A-29C depict schematic cross-sectional views of the rotary piston for volume control of the reservoir E, where FIG. 29A is the minimum capacity stage and FIG. 29C is the maximum volume capacity stage of the reservoir.

DETAILED DESCRIPTION OF THE INVENTION

The present invention relates to a membrane specially developed for use in chambers for artificial circulatory assistance. The membrane circular sections of the present invention may vary in size or not depending on the function to be performed and are interconnected with each other so that the transition between one section and the other is smooth, regardless of the size of each section. Therefore, the size of the sections and the shape adopted by the membrane are essential to define the type of function that it can perform and in which activities it can be used, as will be detailed later.

Figure 9:
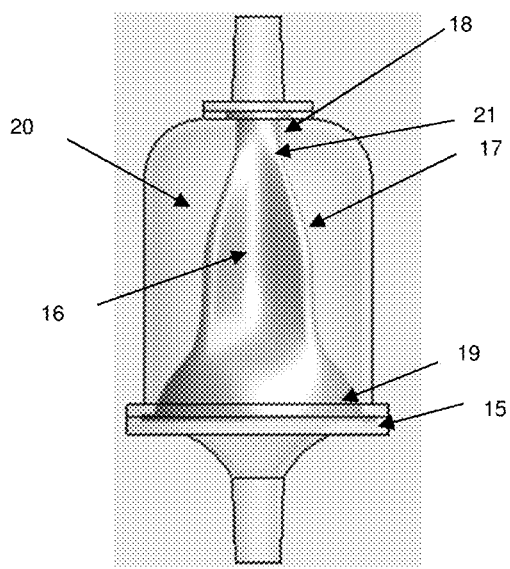
FIGS. 9, 10 and 11 respectively illustrate, in front, perspective and top view, a chamber comprising the arterial pulse wave damping membrane according to the present invention.
Figure 10:
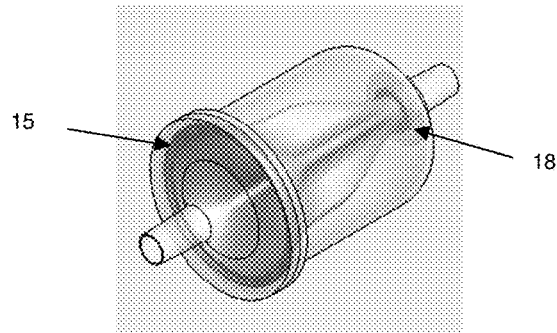
Figure 11:
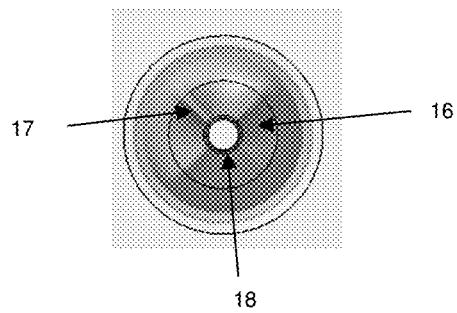

In one embodiment, the present invention discloses a membrane to be used for arterial pulse wave dampening, wherein said membrane comprises a circular base (19) provided with a securing tab (15) from where it protrudes into a conical trunk section (20) which narrows forming recesses (16) and alternating vertical edges (17) to its upper end (21) provided with tab (18) for fixing at its opposite end, as can be seen in FIGS. 9 to 11.

In this configuration the diameter D1 of the circular base (19) is greater than the diameter D2 of the body (20) which is greater than the diameter D3 of the upper end (21) and the perimeter P1 of the circular base (19) is greater than or equal to the perimeter P2 of the conical trunk section (20) which is greater than or equal to the perimeter P3 of the upper end (21).

The recesses (16) and edges (17) formed by the narrowing of the conical trunk section allow the inside of the membrane to adopt the shape of a cross or star with at least 3 points, when in an empty position, as may be observed in FIGS. 12C$a$-12F$a$ and in items A to D of FIGS. 13A$a$-13D$a$. From the recesses (16) and edges (17) the membrane is capable of varying its internal volume without there being any distension or contraction of the membrane, however, without providing additional resistance to movement and without generating stagnant flow points, as can be seen in FIGS. 12A$a$-12F$a$ and 13A$a$-13F$a$.

Arterial pulse waveform damping membranes according to the present invention can be used both to damp negative pressure and positive pressure. For damping the positive pressure, the membrane should be positioned so that the inlet of the flow is made by the base (19) and the outlet by the upper end of the membrane (21) and the shape of the membrane should be adjusted to its initial empty shape. For damping the negative pressure, the membrane should be positioned so that the inlet of the flow is made by the upper end (21) and the outlet by the base of the membrane (19), and the shape of the membrane should be adjusted to its full initial shape.

FIGS. 14A and 14B show the membranes for damping at their maximum (FIG. 14A) or minimum (FIG. 14B) volume capacity. Therefore, the figure represents the "resting" position of the negative pressure damping membrane (FIG. 14A), which is at rest when full, and the "resting" position of the positive pressure damping membrane (FIG. 14B), which is at rest when empty.

In another embodiment, the present invention discloses a pumping membrane comprising a circular base (33) provided with a securing tab (37), from which projects into a cylindrical section (34) formed of recesses (38) and edges (39) alternating to its upper end (35) provided with tab (36) for attachment at its opposite end, as can be seen in FIG. 18.

In the new configuration, the diameters of the circular base (33), the cylindrical section (34) and the upper end (35)

are the same. The perimeters of the circular base (33), the cylindrical section (34) and the perimeter of the upper end (35) are also the same, forming a cylinder.

The recesses (38) and edges (39) of the cylindrical section (34) allow the inside of the membrane to adopt the cross or star shape with at least 3 points when in an empty position. From said recesses (38) and edges (39) the membrane is capable of varying its internal volume without there being any distension or contraction of the membrane, thus without offering additional resistance to the movement and without generating points of stagnation of the flow, as can be observed in FIGS. 19A*a*-19F*b*.

The membranes of the present invention should be made of completely impermeable, flexible and non-elastic material. In this way, they are able to solve the known problems in the prior art involving membranes produced of elastic material.

When the membrane is comprised of elastic material the operation of the device is based on the distension of the elastic membrane which can lead to various problems. In this type of membrane, when the piston aspirates air from inside the outer chamber, the membrane dilates, aspirating blood into the inner chamber (FIG. 7*a*).

The fact that the membrane is not made of resilient material and has recesses (16) and edges (17) consists in a great advantage for blood flow as it allows the membrane to deform without any distension or contraction of its wall. In addition, the membrane is shaped so that its final shape, when filled, is similar to the shape of a bell. This format allows the flow and total renovation of the membrane contents, avoiding the formation of stagnation points, as can be seen in FIG. 7*a*. Therefore, blood flow is continuous and there is no accumulation of volume in the membrane, preventing the formation of thrombi.

In an elastic membrane, for the dilation to occur, the piston has to overcome the elastic force of the membrane, which opposes the distension, which happens only when the force applied to overcome the elastic force exceeds a certain value, in order to the distension occurs abruptly and uncontrolled. As a result of this behavior, the flow and pressure curve in the aspiration phase shows an initial delay and then a sharp peak (FIGS. 8A and 8B). This effect is detrimental to the venous system of the patient, as it can generate the collapse of the veins and even hemolysis.

Additionally, at the infusion phase, the opposite occurs. That is, when the piston begins to infuse, the elastic force comes into action and the volume contained in the internal compartment of the membrane is expelled abruptly, generating a peak of flow and pressure at the outlet (FIGS. 8A and 8C). This effect is also detrimental to the patient because, in addition to the peak of pressure to bring risks to the patient, there is an interruption of the flow during the aspiration phase, which can generate ischemia due to lack of oxygenation.

Another disadvantage presented by devices using elastic material membranes is related to the adjustment of the volume pumped at each beat. The accuracy of the system is greatly impaired, especially at low volumes, because the air flow generated by the piston may not be sufficient to overcome the elastic force, and therefore, there will be no flow. In addition, the elasticity of the membrane changes over time and therefore use the volume infused, and especially the flow and pressure curves may change throughout the procedure.

Figures 23A, 23B:
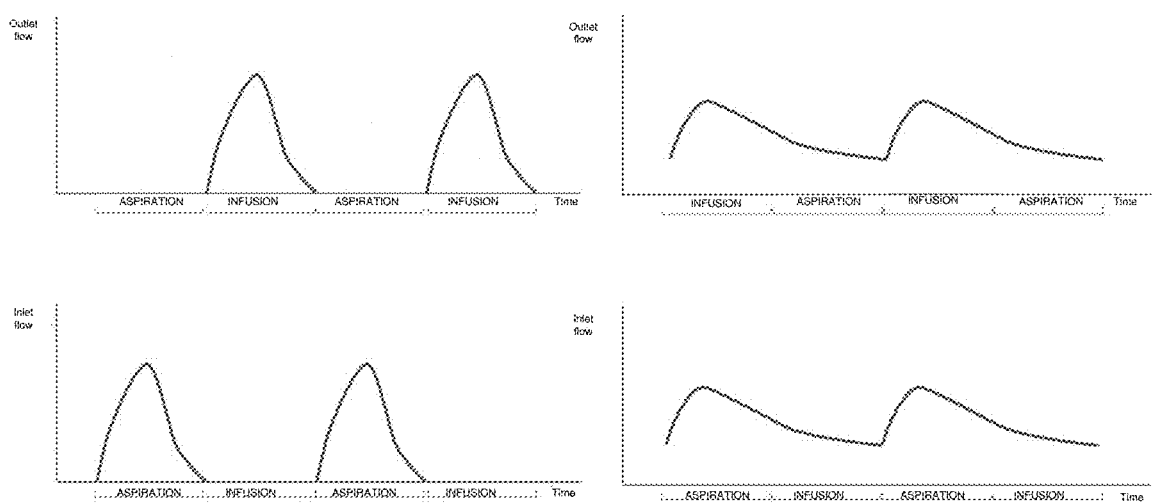
FIG. 23$a$ graphically depicts the behavior of the inflow and outflow during the aspiration and infusion phase for a pulsatile pumping device according to the devices available from the prior art.

Another major problem presented by the membranes of the prior art when used as cardiopulmonary bypass devices is that the flow and pressure curves present a marked peak, well above the patient's physiological pressure during the injection phase (systole) and absence of flow and pressure during the aspiration phase (diastole) (FIG. 23*a*). These characteristics are extremely detrimental to the patient because the excessive pressure peak can damage the blood vessels and expose the patient to the same risks of systemic hypertension and the absence of flow and pressure is even more deleterious as it can cause ischemia. Likewise, the device generates negative pressure peaks and no flow at the pump inlet, which can lead to problems such as collapsing the patient's venous system and even damage to the blood vessels.

In contrast, the membranes of the present invention, since they are not formed from elastic materials, and have a preformed shape, do not suffer from the problems of the prior art, providing a safer and more efficient alternative for the patient (FIG. 23*b*).

The vascular system is distensible, that is, it is able to accommodate more blood volume in its compartment by the variation of vascular tone. In the arteries allows the pulsating heart rate to be accommodated, causing the peak pressure to be attenuated and the blood flow to the small vessels to be continuous and uniform even with minimal pulsations, this property is complacency. Arterial compliance decreases with advancing age, which accentuates the effects of arterial hypertension. The lower the compliance of the arterial system, the higher the pressure increase will be for a given systolic volume. These two physical phenomena distinctive of the cardiovascular system are important factors in the regulation of blood pressure and cardiac output.

From this concept it was possible to develop several possible applications for the membranes of the present invention, such as to act as a blood pumping device, aortic counterpulsation, systolic pressure damping and diastolic pressure assistant.

The present invention further discloses chambers for artificial circulatory assistance utilizing the membranes of the present invention.

In one embodiment, illustrated by FIG. 15, there is disclosed an artificial circulatory assistance chamber comprising a rigid cocoon (27), with a cylindrical body with base (22) and a dome (23), provided with inlet connectors (24) and blood outlet (25) positioned in series, wherein said chamber internally comprises an impermeable membrane (26) dividing the interior of the rigid cocoon (27) into a blood compartment (28) and an external compressible compartment (29) which is filled with gaseous volume. Said chamber is used as an arterial pulse wave damping device.

A pulse damper acts by absorbing the pressure peaks generated by the pump and thus allows to smooth the pressure curve, stabilizes the flow oscillations, producing linear and constant hydraulic flow. Generally, it is formed by a volume chamber mounted attached in the line of hydraulic pipe, has an internal space to absorb volume and pressure. This internal space is filled with a certain volume of gas isolated by means of an elastic membrane. The pressure variation in the hydraulic circuit during pumping acts on the chamber and generates compression of its volume of air during the peak of pressure produced by the pump, this causes the chamber to retain part of the flow volume generated by the pumping at the moment of the pressure peak, the internal air of the chamber is compressed and thereby accumulates pressure. This pressure will be returned to the circuit in the aspiration phase of the pump at the time of the pumping cycle in which the pressure in the circuit becomes lower than the pressure accumulated by the compressed air.

The gas thermodynamics says that "when a gas is compressed by an external pressure, the medium loses energy and the system gains, at the same time, when it expands against an external pressure of the medium, it spends energy in the form of work to carry out the expansion. In this case, the system loses energy, and by the law of energy conservation, the medium gains the same amount". This concept is applied to devices available on the market for the application in various pumping circuits of volumetric displacement drives. But there is no use in medicine in the field of medical devices because, due to the configuration of these devices, coagulation and hemolysis among other problems would be unavoidable.

At this configuration, the blood flow internally traverses the blood compartment (28) of the membrane (26) and transmits pressure and volume to the outer compartment (29) which is at the periphery, thereby reproducing two vascular system properties, distensibility and aortic capacitance.

As discussed previously for the membranes, the chambers for use as arterial pulse wave damping devices of the present invention may be used for negative or positive pressure damping, varying only in the positioning of the chamber relative to blood flow and its initial format.

The artificial circulatory assistance chamber object of the present invention may be produced in biocompatible material, which allows it to be used as an implantable device, which can be removed at any time, unlike RSD treatment which promotes permanent damage to the innervation of the renal artery as well as sympathectomy. In addition, the artificial circulatory assistance chamber object of the present invention promotes the following effects and advantages:
  (i) optimizes vascular distensibility and aortic capacitance by dampening the systolic pressure peak and absorbing blood volume,
  (ii) diastolic pressure increases—in diastole the chamber releases to circulation the volume and pressure absorbed in the systolic,
  (iii) minimizes peripheral vascular resistance, perceived by the heart,
  (iv) minimizes blood pressure,
  (v) minimizes the after-load work of the heart, and
  (vi) increases the cardiac output.

In general, the artificial circulatory assistance chamber object of the present invention, by providing the above-mentioned effects, reduces the occurrence risk of complications inherent to the disease, such as stroke, acute myocardial infarction (AMI) and other morbidity states, also reducing the mortality rate associated with hypertension.

First Variant Form:

The artificial circulatory assistance chamber object of the present invention, as shown in FIG. 16, reproduces the reciprocating pumping as well as the heart, with the one-way inlet and outlet valves working to ensure pulsatile flow with systolic and diastolic phase. The cycle is generated by external pneumatic device driven programmed to inflate and deflate the pneumatic compartment of said chamber. To this end, the artificial circulatory assistance chamber comprises the same rigid cocoon (27), preferably made of transparent polycarbonate and cylindrical body, base (22) and dome (23), preferably with concave outer walls, provided with inlet connectors (24) and outlet (25) blood positioned in series, said chamber further provided with respective one-way valves (30, 31). Internally, the artificial circulatory assistance chamber also comprises an impermeable membrane (26) which divides into two compartments the interior of the rigid cocoon (27), being a blood compartment (28), an inner space through which blood flows, and another outer compartment (29) which is filled with compressible gaseous volume, which varies in two defined and alternating occurrence volumes, the purpose of which is to provide, at each cycle, the filling and emptying of said rigid cocoon (27).

The interaction between the pressure variation of the two sides of the impermeable membrane (26) and the work of the series-mounted one-way valves (30, 31) produces kinetic motion similar to the physiological cardiac blood flow as shown in FIGS. 5A and 5B.

The artificial circulatory assistance chamber object of the present invention thus introduces in the cardiopulmonary bypass systems several advantages not yet achieved by those of the prior art, namely, (i) is a device that simulates circulatory physiology, by applying an active pulsatile flow concept, (ii) produces less hemolysis, (iii) eliminates the effects produced by the use of linear flow.

Those skilled in the art will appreciate various other advantages provided by the artificial circulatory assistance chamber object of the present invention when applied in cardiopulmonary bypass (CPB) systems.

For example, the artificial circulatory assistance chamber object of the present invention can be applied as a special blood pumping device where it takes advantage of the energy of the arterial pulse wave to generate optimized diastolic arterial flow in a direction contrary to the systolic arterial flow. The compressible gas filling the outer compartment (29) is compressed by the interaction between the pressure variation on the two sides of the membrane (26) and the work of the series-mounted one-way valves (30, 31) producing kinetic blood movement. Thus, it is possible to produce diastolic counterflow, that is, the volume of blood accumulated in the systolic phase in the compressible compartment is restored by the same access during the diastolic phase of the circulation. The pumping flow occurs intermittently, and in a direction contrary to the arterial flow, directly affects the diastolic period taking advantage of the volume and pressure accumulated by the chamber in the systolic period. "Counterflow" is of sufficient intensity to provide circulatory support necessary for dialysis treatment, ultrafiltration and ventilatory assistance. To do so, it must be installed in arterial line, preferably femoral arterial, considering the amplitude of the pulse wave of this artery.

It will be apparent to those skilled in the art in this embodiment that the artificial circulatory assistance chamber object of the present invention will produce the following advantageous effects:
  single arterial access, so it is possible to reduce the patient's exposure to a new puncture, reducing the risks and complications inherent to this procedure;
  counterpulsation, it being possible to attenuate the systolic pressure peaks with the performance of the compressible compartment in allowing the accumulation and volume within the systolic phase functioning as a coagulant of aortic compliance and, consequently, in the diastolic phase, the circulation returns the volume compartmentalized in the systolic phase, thus producing an important increase in the flow and diastolic pressure capable of producing counterflow in the arterial access line;
  removes the exposure of the blood in treatment to the trauma produced by the roller pumps;—eliminates the arteriovenous shunt produced by this type of line, the shunt deviates part of the arterial flow, and this deviation decreases blood flow from the accessed arterial bed leading to risks of ischemia and, in more severe cases, can lead to limb amputation;

produces increased blood flow in the vessel accessed;
uses the energy of the patient's own circulation for its operation without the need for electromechanical systems.

Second Variant Form:

The artificial circulatory assistance chamber object of the present invention may also assume a second structural embodiment, such as that shown in FIG. 17, when applied as a ventricular assist device, by partial or total replacement of blood pumping function in patients with insufficient cardiac function and indication for treatment by mechanical circulatory assistance.

In this embodiment, the artificial circulatory assistance chamber object of the present invention comprises the same rigid cocoon (27), preferably made of transparent polycarbonate and cylindrical body, base (22) and dome (23) with concave outer walls, provided with blood inlet (24) and outlet (25) connectors, in addition to respective one-way valves (30, 31), said inlet (24) and outlet (25) connectors being positioned in series. Internally, said chamber comprises an impermeable membrane (26) dividing into two compartments the interior of the rigid cocoon (27), a blood compartment (28), internal space through which blood flows, and another external compartment (29) which is filled with gaseous volume or injectable/aspirable liquid. The gas or liquid is compressed by an external device connected to a perpendicular input (32) by suitable connector. The interaction between the pressure variation on the two sides of the membrane, i.e. the blood compartment (28) and the external compressible compartment (29) together with the work of the series-mounted one-way valves (30, 31) produces kinetic movement similar to physiological cardiac blood flow.

In operation, in this variant embodiment, the blood reaches the chamber for artificial circulatory assistance by the base (22) as a function of the negative pressure generated by the rapid removal of the gas/liquid from the external compressible compartment (29). The chamber fills, the pressure equalizes and the one-way valve (30) of the base (22) closes. The external device projects a certain volume of gas/liquid into the external compressible compartment (29), the gas is compressed and transfers pressure to the blood. The one-way outlet valve (31) in the dome (23) outlet opens allowing blood flow. When the internal and external pressure to the chamber equals, the one-way outlet valve (31) is closed by restarting the cycle.

As is known, during the application of mechanical circulatory assistance devices of the prior art, there are generally some complications. Risk of bleeding, infectious processes, micro-embolisms, formation of thrombi due to the complexity of the procedure or related to the device technical limitation are some examples of complications. Added to these are contraindications, specific conditions in which there is no therapeutic advantage and restriction of vascular access.

The artificial circulatory assistance chamber object of the present invention, structured as illustrated in FIG. 17, simulates circulatory physiology by applying an active, membrane-pumped pulsatile flow concept which simulates the heart pumping mechanism performed by contraction of the heart muscle.

Figure 20:
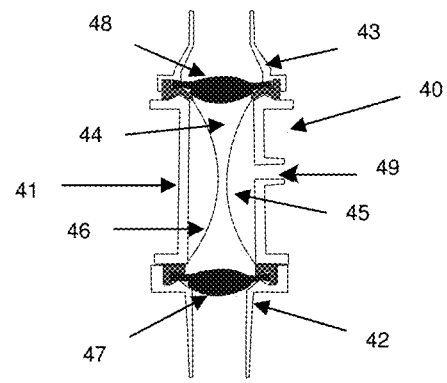
FIG. 20 depicts a schematic cross-sectional view of a variant form of the circulatory assist chamber comprising the membrane according to the present invention.

In another embodiment, the present invention discloses a chamber for artificial circulatory assistance, to be used as a pumping device (FIG. 20). The chamber comprises a rigid cocoon (40), cylindrical body (41) provided with inlet and outlet connectors (43) positioned in series and respective inlet and outlet one-way valves (47, 48). Said chamber internally comprises an impermeable membrane (46), which divides into two compartments the interior of the rigid cocoon (40), a blood compartment (44) and an external compressible compartment (45) which is filled with gaseous volume which is injected or aspirated by an external device connected to an inlet (49) by a suitable connector, said chamber being for use as a pumping device.

In such an embodiment, the gaseous volume in the external compressible compartment (45) varies in two defined and alternating occurrence volumes, providing filling and emptying of the rigid cocoon (40) each cycle, so that the interaction between the pressure change on both sides of the impermeable membrane (46) and the work of the series-mounted one-way valves (47, 48) produces kinetic movement similar to the physiological cardiac blood flow.

The artificial circulatory assistance chambers object of the present invention is compact, small volume, and can be produced in an implantable version, which can be implanted in a paracorporeal or intracavitary manner and are connected to an external driver via the air line with variable length.

In addition, the chambers are equipped with one-way, cartwheel-type valves, which have been specially designed to work with blood. The valves have by characteristic the passage of flow between their radii allowing the blood flow without points of circulation stagnation. They have very low opening pressure, very low reflux, their operation is independent of the spatial position and their movement is self-limited.

Cartwheel-type valves, therefore, solve most of the problems caused by other types of valves, including ball valves and semilunar valves which form stagnation points resulting in the formation and release of thrombi in the circulation.

The artificial circulatory assistance chambers object of the present invention produces less blood trauma because they do not subject blood flow to high speeds, as in centrifugal or crushing pumps, as in roller pumps.

Another great advantage presented by the chambers of the present invention is that they are provided in the way of a single piece and do not require assembly. Accordingly, the present invention provides a solution to the drawbacks encountered in assembling the membranes and their respective devices of the prior art. This is because the assembly procedure of the membrane in a dome, and of the other components, is not a simple and easy operation, and can offer risks of operation, and consequently, physiological risks to the patient if the assembly is not performed correctly.

The present invention further discloses a pump for artificial circulatory assistance which can be applied as in a device for extracorporeal circulation or as a ventricular assistance device by partial or total replacement of blood pumping function in patients with insufficient cardiac function, being indicated for treatment by mechanical circulatory assistance. Said pump comprises the combination of at least two chambers of the invention interconnected in series and having only a one-way inlet valve and a one-way outlet valve.

Figure 21:
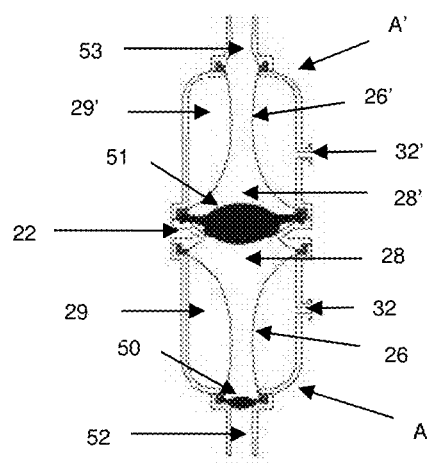
FIG. 21 depicts a schematic cross-sectional view of a variant form of the artificial circulatory assistance pump in accordance with the present invention.

Third Variant Form:

In one embodiment, the artificial circulatory assistance pump object of the present invention may assume a structural configuration such as that shown in FIG. 21. Being formed of two impermeable membrane (A, A') chambers (26, 26') for arterial pulse wave dampening, serially interconnected by the bases (22), but incorporating only one inlet one-way valve (50) and one outlet one-way valve (51).

In this embodiment, chamber A acts in the pumping chamber function and is generally used at the pump inlet, and chamber A' acts in the positive pressure damping chamber function being generally used at the outlet of the pump.

The flow control is regulated by an external pneumatic or hydraulic actuator which aspirates or injects volume into the outer compartment (29) of the chamber (A) through the inlet connector (32).

The operation of the pump is explained by the pressure change of the external compartments (29, 29') of the chambers (A, A'). Aspiration occurs when the pneumatic or hydraulic actuator aspirates air from inside the outer compartment of chamber A, which is initially in a resting state, at its minimum volume capacity. In this step, by aspirating the air from the outer compartment, the membrane aspirates blood from the inlet connector (52) through the lower one-way valve (50), i.e. blood enters the inner compartment (28) of chamber A.

This volume is then transferred through the upper one-way valve (51) into the internal compartment (28') of the membrane (26'). By entering compartment (28'), the blood compresses the membrane (26') which was in its empty resting format, generating compression in the outer compartment (29') and absorbing some of the blood volume. When ejecting the contents from its internal compartment (28), the membrane (26) adopts a new format with minimal volume capacity, as shown in FIG. 12. FIG. 12 depicts the change of the membrane (26) from its minimum capacity (F.4), resting state, up to its maximum volume capacity (A.4).

At the same time, when the membrane (26') has its shape changed upon receiving the injected volume, as shown in FIG. 13, illustrating the change of the membrane (26') from its minimum capacity (A.4), resting state, to its maximum capacity (F.4). The volume injection generates gas compression in the outer chamber (29') of chamber A' and also reduces the volume injected through the outlet connector (53). This effect reduces the amount of blood leaving the pump during the injection phase.

Thus, when the pump stops injecting, the positive pressure generated inside the outer compartment (29') forces the membrane (26') back into its original shape, causing the volume of the inner compartment (28') is injected through the outlet connector (53). This causes blood to flow out of the pump in the aspiration phase.

In this way, the chamber (A') is able to reduce the output flow oscillations, reducing positive pressure peaks and maintaining uninterrupted but pulsating flow being beneficial to the patient, as it reduces the possibility of damage to the arterial system of the patient and the possibility of ischemia, due to lack of flow in the aspiration phase. In addition, the pump reproduces the physiological waveform of the patient's blood pressure.

Figure 22:
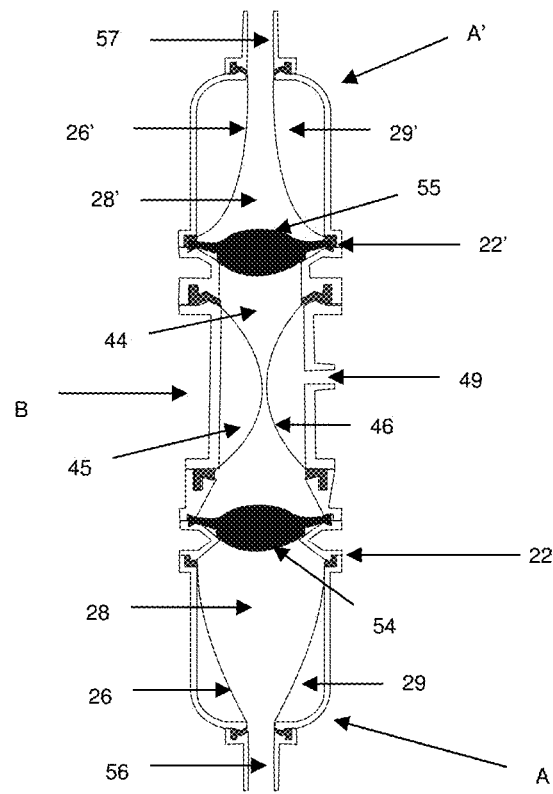
FIG. 22 depicts a schematic cross-sectional view of a second variant form of the artificial circulatory assistance pump in accordance with the present invention.

Fourth Variant Form:

In another embodiment the artificial circulatory assistance pump object of the present invention may also assume a structural configuration such as that shown in FIG. 22. Since the pump object of the present invention is formed by a membrane chamber (B), provided with the membrane (46) positioned between the bases (22, 22') of two membrane chambers (A, A'), provided with the membrane (26, 26') interconnected in series and having only an inlet one-way valve (54) and a one-way outlet valve (55).

In this embodiment, the chamber (A) acts as a negative pressure damper chamber function and is generally used at the pump inlet. The chamber (B) located in the central region of the pump acts on the pumping function. But the chamber (A') acts on the positive pressure damper chamber function and is generally used at the pump outlet.

The operation of the pump object of the present invention in this embodiment can be explained as the following. The flow control is regulated by an external pneumatic or hydraulic actuator which aspirates volume from within the outer compartment (45) of the chamber (B) through the connector (49), reducing the volume of the inner compartment (44).

The chamber (B) when empty (FIG. 19A*a* and FIG. 19A*b*), i.e., when the internal volume is minimal, is in a rest state. With the volume aspiration of the outer compartment (45) of the chamber B, the membrane (46) is changed in shape to increase the available internal volume and enable the volume injection by the cartwheel-type lower one-way valve (54), as shown in FIGS. 19A*a*-19F*b* illustrating the change of the membrane (46) from its minimum capacity (min), resting state, to its maximum volume capacity (max).

As a result, the membrane (26) of chamber A also has its shape changed, as shown in FIGS. 12A*a*-12F*b*, to provide the volume aspirated by chamber B. FIGS. 12A*a*-12F*b* show the change of membrane (26) from its maximum capacity (A), rest state, up to its minimum volume capacity (F). This effect causes the gas to decompress in the outer chamber of chamber A and reduces the volume aspirated through the inlet connector (24), that is, it reduces the amount of blood entering the pump.

Thus, when chamber B stops aspirating volume from chamber A, the negative pressure generated within the outer compartment (29) forces the membrane (26) to return to its original shape, aspirating volume through the inlet connector (56). This causes blood to flow into chamber A in the injection phase. In this way, the chamber is able to reduce incoming flow oscillations, reducing negative pressure peaks and maintaining uninterrupted but pulsating flow. This effect is beneficial to the patient because it reduces the possibility of collapse of the venous system of the patient and possible damage to blood vessels and blood cells.

Then, when the internal compartment (44) is full, the chamber B injects the contents of the inner compartment (44) into the inner compartment (28') of the chamber A' through the upper cartwheel-type one-way valve (55). In this way, the membrane (26') has its shape changed upon receiving the injected volume, as shown in FIGS. 13A*a*-13F*b*, which depicts the changing of the membrane (26') from its minimum capacity (A), resting state, until maximum capacity (F). The volume injection generates gas compression in the outer chamber (29') of chamber A', and also reduces the volume injected through the outlet connector (57). This effect reduces the blood amount leaving the pump during the injection phase.

Thus, when the pump stops injecting, the positive pressure generated inside the outer compartment (29') forces the membrane (26') back into its original shape, causing the volume of the inner compartment (28') is injected through the outlet connector (57). This causes blood to flow out of the pump in the aspiration phase.

Therefore, the chamber (A') is able to reduce output flow oscillations, reducing positive pressure peaks and maintaining uninterrupted but pulsating flow being beneficial to the patient, as it reduces the possibility of damage to the arterial system of the patient and the possibility of ischemia, due to lack of flow in the aspiration phase. In addition, the pump reproduces the physiological waveform of the patient's blood pressure.

As an additional feature, the chambers (A and A') may be provided with a connector in the outer compartment through which gas can be injected or aspirated from their external compartments, so as to adjust the internal volume of air and, consequently, the damping capacity and absorption of the chambers.

In addition, the chambers and pumps of the present invention have the great advantage that the diameter of their inlet and outlet connectors can be made in the diameters of 3/16", 1/4", 3/8" or 1/2", according to the application and the total flow desired, while the internal flow is performed in a larger diameter. A device operating with these diameters throughout its length could provide very high output and input pressure, which could cause damage to the blood cells. With the internal diameter of the pump larger, the behavior of pressures and flows approaches the behavior of pressures and flows within the human heart.

Thereby, the present invention is able to prevent the pressure within the pump from being raised since its internal circuit has a larger gauge and still allows the chambers and pumps of the present invention to be compatible with the tubes used in cardiopulmonary bypass circuits that typically have a 3/16", 1/4", 3/8" or 1/2" internal gauge.

A great advantage of pump pneumatic actuation is that in case of line obstruction, for whatever reason, even if the pump continues to run, there is no flow in the circuit, as the contents of the outlet chamber cannot be expelled due to obstruction and the air volume inside the circuit of the outer compartment of the pumping chamber is constant, the air inside the outer compartment is repeatedly compressed and decompressed without flow in the circuit. Although this condition cannot last for a long time, because the patient cannot run out of blood flow, this characteristic can avoid accidents due to excess pressure in the circuit, such as leaks and rupture of the tubing, besides giving time to the perfusionist to identify the problem that may have caused the obstruction and solve it. Thus, this system is safer than that of the roller pump, for example.

The pneumatic system, on the other hand, also brings another characteristic, which needs to be taken into account in the design of the control system. Because, as the pumping is done by compressing and decompressing air inside a compartment, the flow in the circuit is relatively dependent on the pressure in the line. That is, if the peripheral vascular resistance of the patient or the hydraulic resistance of the system is too high, this may cause air to be compressed inside the outer compartment, reducing the volume of blood pumped. To solve this problem, it is necessary to pump a proportionally larger volume of air, depending on the pressure in the line. Thus, although this system is not as susceptible to changes in line resistance as the centrifugal pump, it is advisable to provide the system with a flowmeter so that any differences between the flow of pumped air and the blood flow in the line are detected and corrected.

Figure 30:
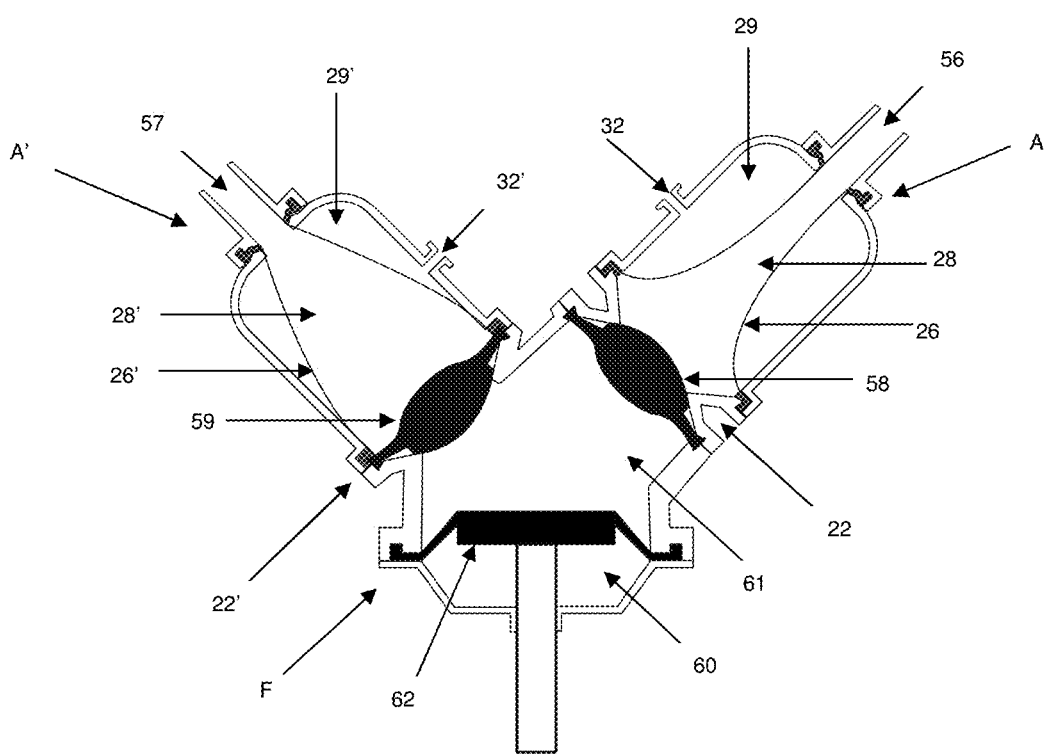
FIG. 30 depicts a schematic cross-sectional view of a variant form of the pump for artificial circulatory assistance in accordance with the present invention.

Fifth Variant Form:

In another embodiment, the artificial circulatory assistance pump object of the present invention may also assume a structural configuration such as that shown in FIG. 30. Since the pump object of the present invention is formed by a membrane pump-type chamber (F), with a direct drive positioned between the bases (22, 22') of two chambers (A, A') provided with a membrane (26, 26'), serially interconnected and having only one inlet one-way valve (58) and one outlet one-way valve (59).

In this embodiment, the operation is similar to that described in the previous embodiment, chamber A acts on the negative pressure dampening chamber function and is generally used at the pump inlet and chamber A' acts on the positive pressure dampening chamber function being generally used at the pump outlet. However, the pumping chamber is replaced by a membrane pump with direct motor drive. The flow control is regulated by the chamber membrane pump motor (F) which controls the volume of the outer (60) and inner (61) compartment of the chamber (F).

In the same manner as the chamber (B), the chamber (F) when empty, i.e., when the internal volume is minimal, is in a rest state. With the actuation of the motor, the membrane (62) has its shape changed so as to increase the available internal volume and enable volume injection by the one-way cartwheel valve (58).

Thereafter, when the internal compartment (61) is full, the chamber (F) injects the contents of the inner compartment (61) into the inner compartment (28') of the chamber A' through the cartwheel one-way valve (59).

The advantage of this embodiment is that since the pump has a direct drive, the blood flow can be predicted more accurately because it does not depend on the resistance in the line. Thus, it is possible to dispense the flowmeter into the control circuit.

Figures 31A, 31B:
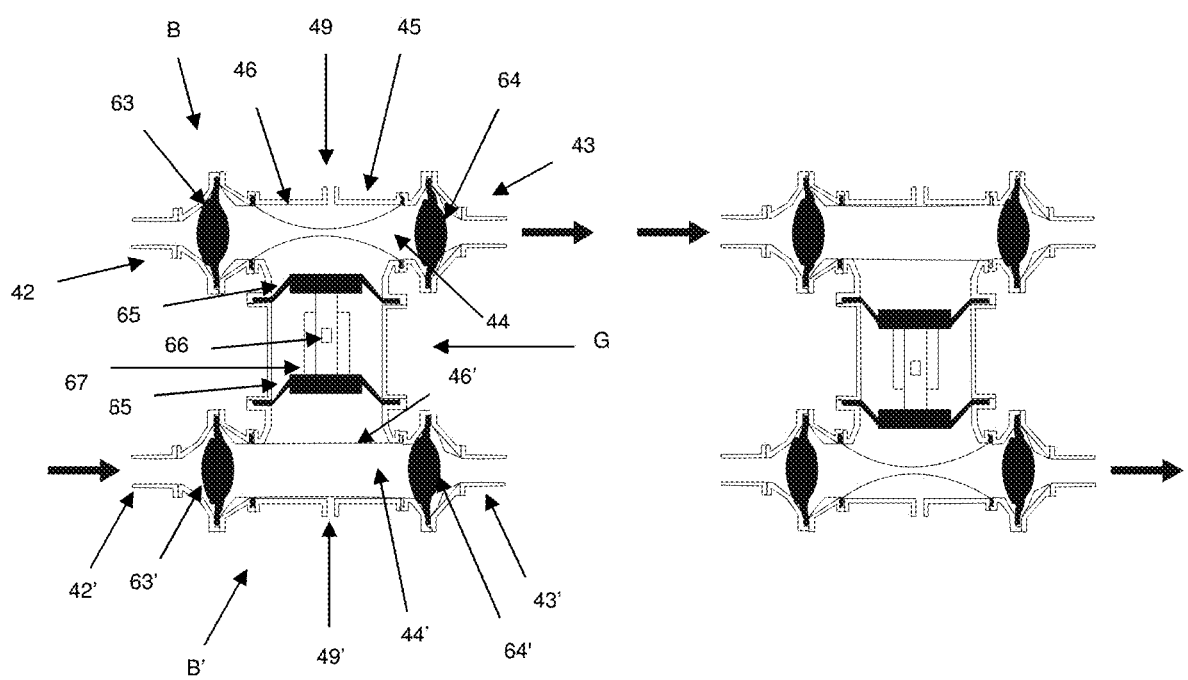
FIG. 31 depicts a schematic cross-sectional view of a variant form of the pump for uninterrupted and constant flow in accordance with the present invention.

Sixth Variant Form:

In another embodiment, the artificial circulatory assistance pump object of the present invention may also assume a structural configuration such as that shown in FIGS. 31A and 31B. Since the pump object of the present invention is formed by a set (G) composed of two membrane pistons (65) coupled to each other by the same shaft (65) with single acting (67), coupled between two chambers (B, B') provided with membranes (46, 46') and having two inlet one-way valves (63, 63') and two outlet one-way valves (64, 64'). This pump works with a single actuator, which should provide alternating motion, preferably at constant speed. In this way, we can obtain uninterrupted and constant flow. As the flow is constant, the pressure is also constant, therefore, for this embodiment, the use of the damping chambers is not required.

Figure 32A:
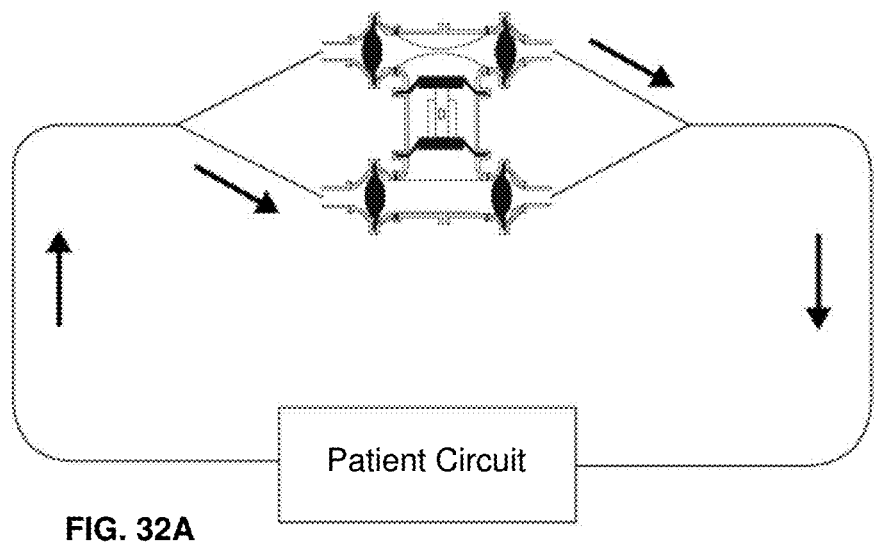
FIGS. 32A and 32B depict the uninterrupted and constant flow pumping system of a preferred variant embodiment.
Figure 32B:
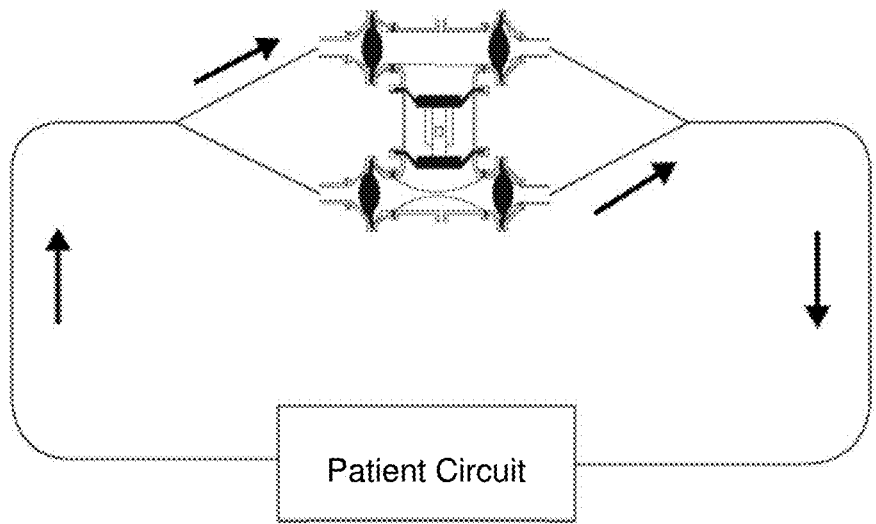

In this embodiment, the pump must be mounted so that the initial position of the membranes (46, 46') is reversed, i.e. when one membrane is in the empty position, the other is in the full position. In addition, the spaces between the piston membranes (65) and the membranes (46, 46') of the pumping chambers should be filled, preferably with sterile saline, to ensure better control of the actuator system and also greater safety in case of accidental rupture of the membrane. Thus, with alternating motion of the actuator, when one chamber (B) is aspirating, the other (B') is infusing. Thus, we will have continuous flow at the pump inlet and outlet of the system, as shown in FIG. 32.

This type of pumping is especially interesting for applications such as hemodialysis and veno-venous ECMO, where there is no great advantage in the pulsatile flow, but due to the long duration of treatment, as in the case of veno-venous ECMO, or of the repeated courses such as in the case of hemodialysis, physiological pumping through membranes and the low rate of damage to blood cells is extremely beneficial to the patient and to treatment. In this system, flow adjustment can be done either by adjusting the volume pumped each cycle or by the pumping frequency.

This system may also be used for other applications such as infusion or aspiration of blood, infusion of cardioplegic solutions with blood or not, as well as for aspiration of blood and discharges from surgical and non-surgical cavities and from airways and oral cavity of the patient. In the specific case of aspiration of blood and discharges during surgery, this system can advantageously replace the aspiration vials as it does not depend on a vacuum source and the drained volume can be packaged in a flexible bag that is cheaper and takes up less space. Thus, if the pumping system has a battery, the system becomes portable, allowing aspiration anywhere.

Figure 24:
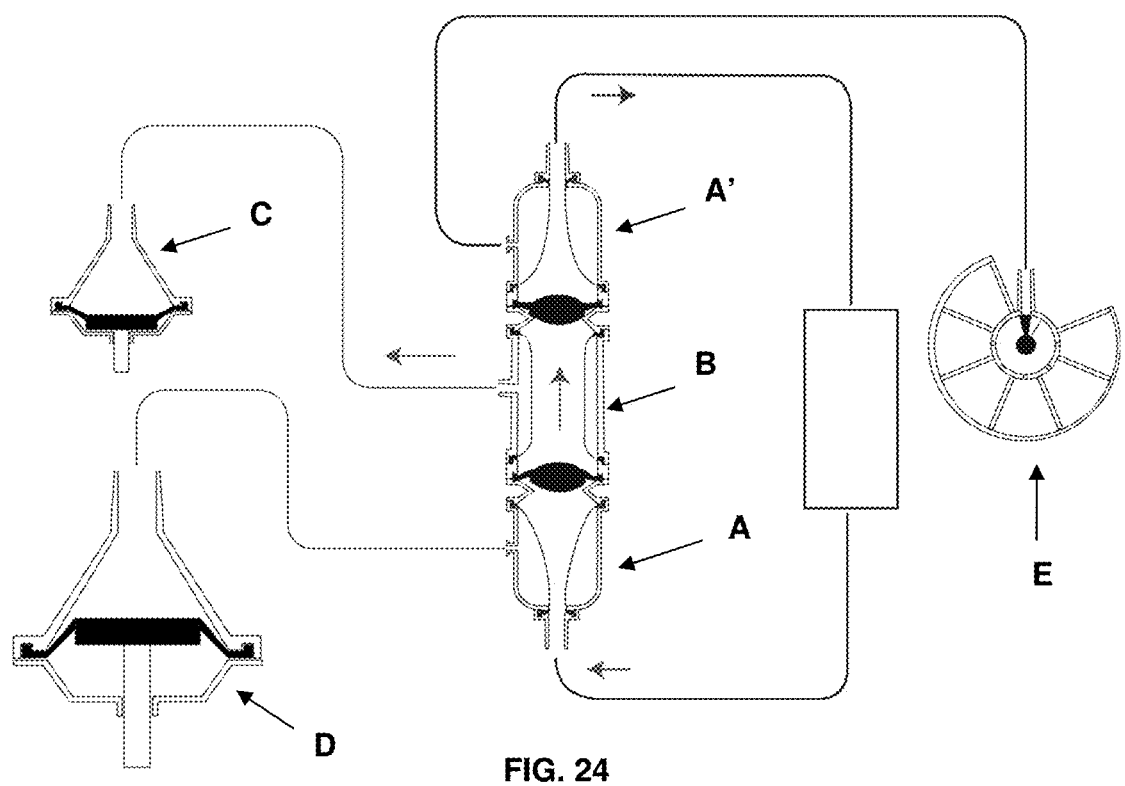
FIG. 24 depicts a schematic cross-sectional view of the complete pumping system, including arterial compliance and venous volume control systems, when air is aspirated from within the outer compartment of chamber B.
Figure 25:
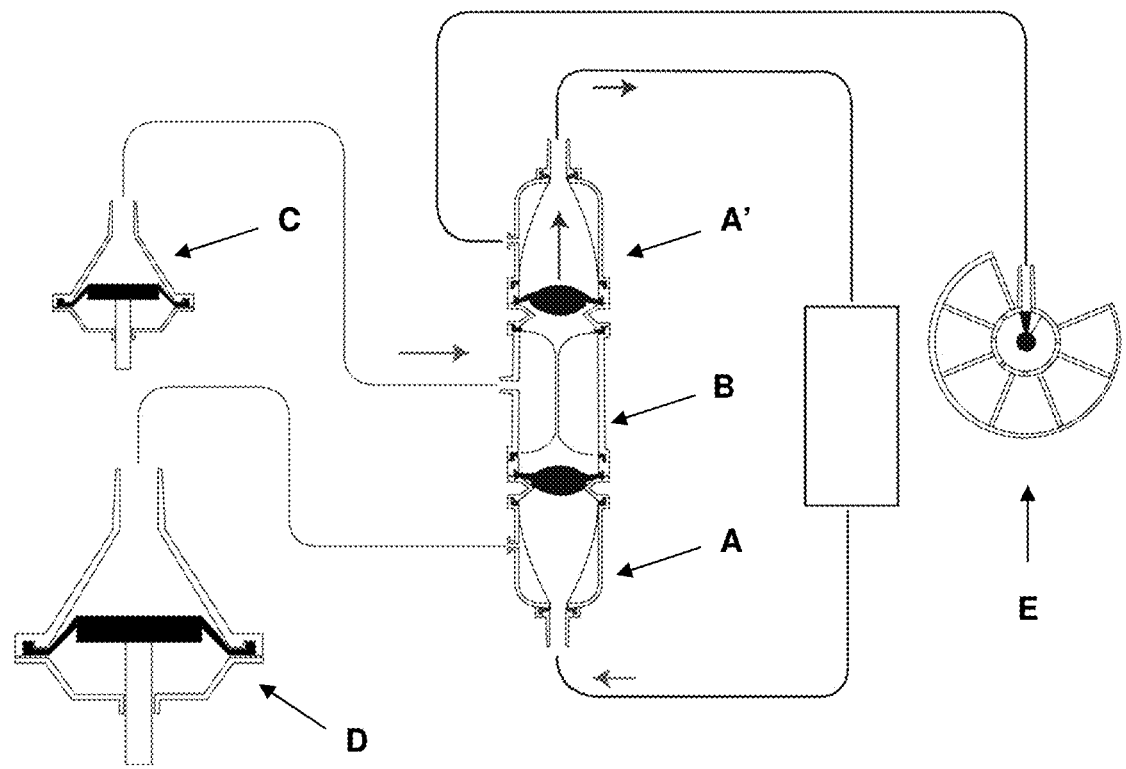
FIG. 25 depicts a schematic cross-sectional view of the complete pumping system, including arterial compliance and venous volume control systems, when air is injected into the outer chamber of chamber B.

The present invention, shown in FIGS. 24, 25 and 26, further deals with a closed pumping system comprising:
a) a cardiopulmonary bypass pump, as described above;
b) an air pump (C) connected to the pumping chamber (B);
c) an air reservoir (D) connected to the inlet chamber (A);
d) an air reservoir (E) connected to the outlet chamber (A').

The air pump (C) is of the piston or membrane type and acts by pumping air into the outer compartment (45) of the pumping chamber (B). said pump works in closed circuit, i.e. the volume of air inside the air-chamber pump system is constant. It is responsible for controlling the beat heart rate and the volume infused with each beat.

So that the beat heart rate is adjusted, the engine rotation speed must be changed. The adjustment of the pumped volume is done with the aid of a system of crankshaft, or similar, that allows the reversion of the direction of rotation and the control of the angle of rotation. Therefore, the motor must be able to rotate alternately to one side and the other, and it must also allow the control of the engine rotation angle. Suitable engine types for the present invention are stepper motors or servo motors, or even any motor that meets such requirements. FIGS. 27A-27E show schematic cross-sectional views of the reversible movement of the piston of said air pump (C).

Therefore, by controlling the direction of rotation and the angle of rotation, air can be alternately aspirated and injected from the outer compartment of the chamber and the stroke of the piston can be controlled, thereby controlling the volume pumped with each beat. The angle of rotation should be at most 180°, corresponding to the maximum stroke of the piston, as can be seen in FIG. 27.

The system air reservoir (D) object of the present invention is of the membrane or cylinder piston type and must have a fixed volume, endless screw mechanism, reversal capacity of the rotation direction and rotation angle control. This piston operates in closed circuit, connected to the negative pressure damping chamber (A) at the pump inlet, with fixed total air volume.

The function of the air reservoir (D) is to adjust the volume and pressure in the circuit. To increase the pressure and increase the volume in the patient circuit, air must be injected within the outer compartment (29) into the chamber. To reduce the pressure and decrease the volume in the patient circuit, air must be aspirated from inside the outer compartment (29) of the chamber. This feature compensates for the volume changes in the patient circuit, as a function of the vasoconstriction or vasodilation of the patient's vascular system, when in a closed circuit.

The air reservoir (E) is a special reservoir allowing the volume of air to be varied within it, without, however, varying the pressure therein. It is coupled to the positive pressure damping chamber (A') and allows the change in the complacency or damping factor of the outlet chamber (A'). FIGS. 29A-29C show schematic cross-sectional views of the rotating piston for volume control of the reservoir E, where "A" is the stage with minimum capacity and "C" is the stage with the maximum volume capacity of the reservoir.

This reservoir is formed by a central cylinder connected by means of holes to several separate compartments. The control of the reservoir volume is carried out by means of a rotary piston which regulates the number of compartments connected to the main cylinder without changing the internal pressure of the reservoir. Therefore, when the piston is turned counterclockwise the compartments are progressively connected to the central cylinder, increasing the volume of the reservoir. When the piston is turned clockwise the effect is reversed, and the compartments are progressively disconnected from the central cylinder, reducing the volume of the reservoir. Control of the reservoir volume through the piston can be seen in FIGS. 28A-28C, which depicts the volume change, FIG. 28A being the minimum capacity and FIG. 28C the maximum capacity of the reservoir.

This feature is especially important for the operation of the positive pressure damping chamber (A') functioning, otherwise we would be interfering with the average pressure of the circuit, which would make controlling the pressure and volume of the system more difficult.

Since the reservoir works with a rotary piston, the mechanism can be coupled directly to the engine shaft. However, the engine should allow reversal of the direction of rotation and precise angle control. To increase the damping factor, the piston must be rotated in order to increase the volume of the reservoir. To decrease the damping factor, the piston must be turned so as to decrease the volume of the reservoir.

FIG. 26 shows a structural variant preferably used for the artificial circulatory assistance chamber according to the present invention. In this embodiment, it is observed that the piston or membrane type pump (C) acting to pump air or liquid into the outer compartment (45) is structurally incorporated in said pumping chamber (B), likewise working in closed circuit, i.e. the volume of air or liquid within the pump-chamber system is constant.

In this embodiment, the system is completely disposable and, for use in cardiopulmonary bypass, the space between the pump membrane (C) and the pumping chamber membrane (B) should preferably be filled with sterile saline solution. In addition, after filling with saline solution, the connector on the top should remain closed.

The operation of such a variant system, which should also be advisable to include pressure transducers and flow sensors, is similar to that of the system shown in FIGS. 24 and 25, but now the engine acts directly on the disposable membrane piston of the pump (C). When the engine pulls the piston downward, the membrane exerts negative pressure inside the outer compartment, causing the pumping membrane to expand, which generates negative pressure within the blood compartment, causing the outlet valve to close and the inlet valve to open and blood enters the pumping chamber. When the engine pushes the piston upwards, the membrane exerts positive pressure inside the outer compartment, causing the pumping membrane to contract, which generates positive pressure inside the blood compartment, causing the inlet valve to close and the outlet valve to open and the blood flows out of the pumping chamber.

With this embodiment illustrated in FIG. 26, the system will offer technical and functional advantages related to a linear and continuous flow path; easier construction; pumping performed by membranes with physiological shape without any restriction or stagnation point; membrane pumping mechanism and direct coupling to the drive system; double insulation since the blood is separated from the external environment by two membranes; pumping membrane fully enclosed by the liquid inside the outer compartment deforming homogeneously and physiologically and reducing the risk of hemolysis and damage to blood cells; coupling the motor membrane with the membrane of the pumping chamber performed through sterile saline solution, which must be filled by the user at the time of installation through the connector on the top of the device that in case of rupture of the membrane, there will be no risk of contamination, nor hemolysis; control ratio of 1:1, i.e. the control of the pumping chamber membrane is immediate and direct with no loss of volume or delay.

In addition to the advantages clearly envisaged by those skilled in the art and described above, in order to avoid subjecting the blood to very large pressure changes, the artificial circulatory assistance chamber according to the present invention has sizes compatible with the heart of an adult, and then, the blood is subjected to physiological pressures even within the pump, reducing the possibility of hemolysis and damage to blood cells commonly found in prior art pumping systems. In addition, at lower pressures within the pumping chamber, the engine of the chamber system for artificial circulatory assistance according to the present invention can be much smaller, thus reducing dimensions, weight and engine consumption, which allows its mounting in a support separate from the main console and very close to the patient, which, in turn, allows to reduce the size of the system tubes and consequently the priming of the circuit.

In addition, in order for the system to incorporate the artificial circulatory assistance chamber according to the present invention to function properly, it is recommended that a console be provided with the following basic features:
- engine with rotation reversal capability and rotation angle control;
- control system for the engine capable of controlling the speed and acceleration of rotation and the angle of rotation;
- mechanical system capable of reversing engine rotation;
- mechanical system capable of converting the engine rotation in alternating linear motion;
- external reservoir with actuator system that allows to change the pressure and the volume of air inside the compartment;
- control systems for actuators of external reservoirs;
- external reservoir with actuator system that allows to change the air volume inside the compartment, without varying the pressure;
- software and hardware capable of controlling and displaying parameters relating to the volume of injection and aspiration; time of injection and aspiration; relation between the time of injection and aspiration; acceleration of movement during injection and aspiration; frequency of beats; estimated mean flow calculation; volume and air pressure inside the external reservoirs.

Optionally, said console may have flow and pressure monitoring capability in the pump and in the circuit and automatically control the pumping parameters, in order to achieve user defined flow and pressure parameters, which may be disposable or pressure sensors or not, positioned inside the chambers and/or inside the reservoirs, to allow better control of the pumping parameters.

The invention claimed is:

1. A pump for artificial circulatory assistance, the pump comprising:
    a membrane chamber including a pumping membrane, an outer compartment, an inner compartment, and a connector, wherein the membrane chamber is arranged between bases of two artificial circulatory assistance chambers, each artificial circulatory assistance chamber being provided with an arterial pulse wave damping membrane;
    a one-way inlet valve arranged between the membrane chamber and a first artificial circulatory assistance chamber of the two artificial circulatory assistance chambers; and
    a one-way outlet valve arranged between the membrane chamber and a second artificial circulatory assistance chamber of the two artificial circulatory assistance chambers,
    wherein the pumping membrane includes a first circular base provided with a first
    securing tab, from which the pumping membrane projects into a cylindrical section formed of recesses and edges alternating to an upper end of the pumping membrane provided with a first tab for attachment at an opposite end of the first securing tab, wherein a diameter of the first circular base and a diameter of the upper end are equal, wherein a perimeter of the first circular base, a perimeter of the cylindrical section, and a perimeter of the upper end are the same to form a cylinder, and wherein an inside of the pumping membrane adopts a cross or star shape with at least 3 points when in an empty position,
    wherein each of the two artificial circulatory assistance chambers comprise a rigid cocoon, with a cylindrical body with a base and a dome, provided with an inlet connector and an outlet connector positioned in series, wherein each of the two artificial circulatory assistance chambers internally comprises an impermeable membrane dividing an interior of the rigid cocoon into a blood compartment and an external compressible compartment which is filled with a gaseous volume,
    wherein the arterial pulse wave damping membrane comprises a second circular base provided with a second securing tab from where the arterial pulse wave damping membrane protrudes into a conical trunk section which narrows forming recesses and alternating vertical edges to an upper end of the arterial pulse wave damping membrane provided with a second tab for fixing at an opposite end of the second securing tab,
    wherein a diameter of the second circular base is greater than a diameter of the conical trunk section which is greater than a diameter of the upper end of the arterial pulse wave damping membrane, and a perimeter of the second circular base is greater than or equal to a perimeter of the conical trunk section which is greater than or equal to a perimeter of the upper end of the arterial pulse wave damping membrane, and
    wherein the recesses and alternating vertical edges formed by the narrowing of the conical trunk section allow an inside of the arterial pulse wave damping membrane to adopt a shape of a cross or star with at least 3 points, when in an empty position.

2. The pump according to claim 1, wherein the two artificial circulatory assistance chambers have a connector configured for injection and aspiration of a gas in the external compressible compartment.

3. The pump according to claim 1, wherein the one-way inlet valve and the one-way outlet valve are a cartwheel type.

4. The pump according to claim 1, wherein a gauge of each of the inlet connector and the outlet connector has a diameter of 3/16 inch to 1/2 inch.

5. The pump according to claim 4, wherein the gauge each of the inlet connector and the outlet connector is 3/8 inch.

6. The pump according to claim 1, wherein the pump is a device for cardiopulmonary bypass to pump a blood flow.

7. The pump according to claim 1, wherein the pump is a ventricular assistance device for partial or total replacement of a blood pumping function in a patient.

8. A pump system, comprising:
the pump according to claim 1 for cardiopulmonary bypass to pump a blood flow;
an air or liquid pump connected to the membrane chamber;
a first air reservoir connected to the first artificial circulatory assistance chamber; and
a second air reservoir connected to the second artificial circulatory assistance chamber.

9. The pump system according to claim 8, wherein the pump system is a closed system.

10. The pump system according to claim 9, wherein the air or liquid pump is configured to convert a rotation of a motor into alternating linear motion.

11. The pump system according to claim 8, further comprising a software and a hardware configured to control and display parameters on an injection and aspiration volume, a time of injection and aspiration, a relation between the time of injection and aspiration, an acceleration of movement during injection and aspiration, a frequency of beats, an estimated mean flow calculation, and a volume and air pressure inside external reservoirs.

12. The pump system according to claim 8, wherein the air or liquid pump is a piston or membrane type.

13. The pump system according to claim 12, wherein the piston type is configured to reverse rotation and control an angle of rotation.

14. The pump system according to claim 13, wherein the control of the angle of rotation is up to 180 degrees.

15. The pump system according to claim 12, wherein the air or liquid pump allows a rotation of a motor to be reversed.

16. The pump system according to claim 8, wherein the first air reservoir is a membrane or cylinder piston type.

17. The pump system according to claim 16, wherein the first air reservoir is configured to change a pressure and volume of air within the outer compartment.

18. The pump system according to claim 8, wherein the second air reservoir is configured to change a volume of air within the second air reservoir, without changing a pressure.

19. The pump system according to claim 8, wherein the air or liquid pump is structurally incorporated in the membrane chamber by working in a closed circuit so that a volume of the air or liquid within the pump system is constant.

20. The pump system according to claim 19, wherein a space between a membrane of the air or liquid pump and the pumping membrane of the membrane chamber is filled with a sterile saline solution.

21. A pump for artificial circulatory assistance, the pump comprising:
a membrane pump-type chamber including a direct drive provided with a membrane, the membrane pump-type chamber being arranged between bases of two artificial circulatory assistance chambers, each of the artificial circulatory assistance chambers being provided with an arterial pulse wave damping membrane;
a one-way inlet valve arranged between the membrane pump-type chamber and a first artificial circulatory assistance chamber of the two artificial circulatory assistance chambers; and
a one-way outlet valve arranged between the membrane pump-type chamber and a second artificial circulatory assistance chamber of the two artificial circulatory assistance chambers,
wherein each of the two artificial circulatory assistance chambers comprise a rigid cocoon, with a cylindrical body with a base one of the bases and a dome, provided with an inlet connector and an outlet connector positioned in series, wherein each of the two artificial circulatory assistance chambers internally comprises an impermeable membrane dividing an interior of the rigid cocoon into a blood compartment and an external compressible compartment which is filled with a gaseous volume,
wherein the arterial pulse wave damping membrane comprises a circular base provided with a securing tab from where the arterial pulse wave damping membrane protrudes into a conical trunk section which narrows forming recesses and alternating vertical edges to an upper end of the arterial pulse wave damping membrane provided with a tab for fixing at an opposite end of the securing tab,
wherein a diameter of the circular base is greater than a diameter of the conical trunk section which is greater than a diameter of the upper end, and a perimeter of the circular base is greater than or equal to a perimeter of the conical trunk section which is greater than or equal to a perimeter of the upper end, and
wherein the recesses and alternating vertical edges formed by the narrowing of the conical trunk section allow an inside of the arterial pulse wave damping membrane to adopt a shape of a cross or star with at least 3 points, when in an empty position.

22. The pump according to claim 21, wherein the membrane of the direct drive is fitted inside a cocoon in a fixed airtight manner.

23. The pump according to claim 21, wherein the membrane of the direct drive is made of a flexible and non-elastic material.

24. A pump system, comprising:
the pump according to claim 21 for cardiopulmonary bypass to pump a blood flow;
a first air reservoir connected to the first artificial circulatory assistance chamber; and
a second air reservoir connected to the second circulatory assistance chamber.

25. A pump for artificial circulatory assistance, the pump comprising:
a set composed of two membrane pistons coupled to each other by a shaft with single acting, coupled between two membrane chambers, each of the two membrane chambers being provided with pumping membranes;
a first one-way inlet valve arranged between a first inlet and a first membrane chamber of the two membrane chambers; and
a second one-way inlet valve arranged between a second inlet and a second membrane chamber of the two membrane chambers;
a first one-way outlet valve arranged between the first membrane chamber and a first outlet;
a second one-way outlet valve arranged between the second membrane chamber and a second outlet,
wherein each of the two membrane chambers includes an outer compartment, an inner compartment, and a connector,
wherein a space between the membrane pistons and the pumping membranes is filled with a sterile saline, wherein an initial position of each membrane is reversed,
wherein each pumping membrane includes a circular base provided with a securing tab, from which the pumping membrane projects into a cylindrical section formed of recesses and edges alternating to an upper end of the pumping membrane provided with a tab for attachment at an opposite end of the securing tab, wherein a diameter of the circular base and a diameter of the upper end are equal, and wherein a perimeter of the circular base, a perimeter of the cylindrical section, and a perimeter of the upper end are the same to form a cylinder, and
wherein an inside of the cylindrical section adopts a cross or star shape with at least 3 points when in an empty position.

* * * * *